(12) United States Patent
Agris et al.

(10) Patent No.: US 7,901,892 B2
(45) Date of Patent: Mar. 8, 2011

(54) METHODS AND COMPOSITIONS FOR DETERMINING THE PURITY OF CHEMICALLY SYNTHESIZED NUCLEIC ACIDS

(75) Inventors: Paul F. Agris, Raleigh, NC (US); Christopher D. J. Pearce, Surrey (GB); Lloyd G. Mitchell, Durham, NC (US)

(73) Assignee: North Carolina State University, Raleigh, NC (US)

( * ) Notice: Subject to any disclaimer, the term of this patent is extended or adjusted under 35 U.S.C. 154(b) by 1356 days.

(21) Appl. No.: 10/190,795

(22) Filed: Jul. 8, 2002

(65) Prior Publication Data

US 2003/0044831 A1 Mar. 6, 2003

Related U.S. Application Data

(63) Continuation of application No. 09/747,467, filed on Dec. 22, 2000, now Pat. No. 6,929,907, which is a continuation-in-part of application No. 09/476,975, filed on Dec. 31, 1999, now abandoned.

(51) Int. Cl.
*G01N 33/53* (2006.01)
(52) U.S. Cl. .............................. 435/7.1; 435/6
(58) Field of Classification Search ............. 435/6, 91.2, 435/91, 287.2
See application file for complete search history.

(56) References Cited

U.S. PATENT DOCUMENTS

| 5,049,656 | A |   | 9/1991  | Lewis et al. |
|-----------|---|---|---------|--------------|
| 5,221,736 | A |   | 6/1993  | Coolidge et al. |
| 5,464,759 | A | * | 11/1995 | Coolidge et al. ............. 435/91.2 |
| 5,489,678 | A |   | 2/1996  | Fodor et al. |
| 5,744,101 | A |   | 4/1998  | Fodor et al. |
| 5,843,644 | A |   | 12/1998 | McGall |
| 5,871,747 | A |   | 2/1999  | Gengoux-Sedlik et al. |
| 6,017,496 | A |   | 1/2000  | Nova et al. |
| 6,107,039 | A |   | 8/2000  | Hanna |
| 6,852,487 | B1 | * | 2/2005 | Barany et al. .................. 435/6 |
| 2002/0097900 | A1 | * | 7/2002 | Arena et al. ................ 382/129 |
| 2002/0150921 | A1 | * | 10/2002 | Barany et al. .................. 435/6 |
| 2003/0059094 | A1 | * | 3/2003 | Cattell et al. ................ 382/128 |
| 2003/0224382 | A1 | * | 12/2003 | McClelland et al. ............ 435/6 |

FOREIGN PATENT DOCUMENTS

| EP | 0 906 917 A2 | 4/1999 |
| JP | 11-80185 A | 3/1999 |
| WO | WO 98/03532 | 1/1998 |

OTHER PUBLICATIONS

Schena et al. PNAS 1996 vol. 93, p. 10614-10619.*
Degling, Lena, et al., *Biodegradable microspheres XVIII: the adjuvant effect of polyacryl starch microparticles with conjugated human serum albumin, Vaccine*, vol. 13, No. 7, pp. 629-636.
International Search Report, International Application No. PCT/US00/35600 dated Apr. 17, 2001.
Andrews et al. "Analysis of DNA adducts using high-performance separation techniques coupled to electrospray ionization mass spectrometry" Journal of Chromatography, vol. 856, No. 1-2, (Sep. 24, 1999), pp. 515-526.
Chersi et al. "Preparation of Rabbit Antibodies to 4 4' Dimethoxytriphenylmethyl the Prosepective Goup in Oligonucleotide Synthesis" Biological Chemistry Hoppe-Seyler, v. 372, No. 9, 1991, pp. 845-848.
Hashizume et al: "Specificity of anti-polynucleotide monoclonal antibodies from human-human hybridomas." In Vitro Cellular & Developmental Biology: Journal of the Tissue Culture Association, v. 23, No. 1, 1987, pp. 53-56.
Supplemental Partial European Search Report, EP 00 99 0402 mailed May 11, 2004.
Partial European Search Report, EP 08 00 6268, issued Jun. 5, 2008.
Weiler J et al. Combining the preparation of ligonucleotide arrays and synthesis of high-quality primers. Analytical Biochemistry. Dec. 15, 1996;243(2):218-227.
Fodor S P A et al. Light-directed, spatially addressable parallel chemical synthesis. Science. Feb. 15, 1991;251(4995):767-773.
Andrews et al.; "Analysis of DNA adducts using high-performance separation techniques coupled to electrospray ionization mass spectrometry" *Journal of Chromatography A* 856 515-526 (1999).
Chersi et al.; "Preparation of Rabbit Antibodies to 4,4'-Dimethoxytriphenylmethyl, the Protective Group in Oligonucleotide Synthesis" *Biol. Chem. Hoppe-Seyler* 372 845-848 (1991).
Hashizume et al; "Specificity of Anti-Polynucleotide Monoclonal Antibodies From Human-Human Hybridomas" In Vitro Cellular & Development Biology 23:1 53-56 (1987).
European Search Report for Application No. PC/JM/P12326EP; Dated Nov. 5, 2004.

* cited by examiner

*Primary Examiner* — Jacob Cheu
(74) *Attorney, Agent, or Firm* — Myers Bigel Sibley & Sajovec, P.A.

(57) ABSTRACT

This application describes an antibody that specifically binds to a synthetic oligomer (e.g., an oligonucleotide or oligopeptide) having a organic protecting group covalently bound thereto, which antibody does not bind to that synthetic oligomer when the organic protecting group is not covalently bound thereto. Methods of making and using such antibodies are also disclosed, along with cells for making such antibodies and articles carrying immobilized oligomers that can be used in assay procedures with such antibodies.

12 Claims, 10 Drawing Sheets

METHODS AND COMPOSITIONS FOR DETERMINING THE PURITY OF CHEMICALLY SYNTHESIZED NUCLEIC ACIDS

RELATED APPLICATIONS

This application is a continuation of the commonly owned, application Ser. No. 09/747,467, filed Dec. 22, 2000, now U.S. Pat. No. 6,929,907 which is a continuation-in-part of commonly owned, application Ser. No. 09/476,975, filed Dec. 31, 1999, now abandoned the disclosures of both of which are incorporated by reference herein in their entirety.

FIELD OF THE INVENTION

The present invention concerns the detection, identification and quantification of protecting groups remaining after chemical synthesis of oligomers, particularly oligonucleotides.

BACKGROUND OF THE INVENTION

Over the past decade automated chemical synthesis of nucleic acids such as DNA and RNA on solid supports has been developed. These chemical processes include the use of agents to protect the exocyclic amines of the nucleotide bases adenine, thymine, cytosine and guanine and to direct the synthesis by blocking the 2'OH of RNA's ribose. The bases within the nucleic acid product of the synthesis are deprotected upon cleavage of the nucleic acid from the solid support. However, the extent of base deprotection is not easily determined.

For example, after base deprotection of synthetic RNA, products still contain the 2'-dimethylsilyl tert-butyl group as a protection of the 2'OH of the ribose moiety. This protecting group is removed carefully by chemical means so as not to effect the chemistry and structure of the RNA. However, the extent of deprotection of the 2'OH is not readily determined. The nucleic acid is purified by high pressure liquid chromatography or by gel electrophoresis. However, some of the unwanted products of the synthesis are complete nucleic acid sequences that still contain one or more protecting groups, and shorter than full length (aborted) sequences difficult to separate from full length sequences, especially for oligomers of longer than 50 nucleosides. At present, there is no easy method to determine how much of each protecting group, if any, still remains on the product, and what proportion of the product is full-length. See generally Davis, G. E., Gehrke, C. W., Kuo, K. C., and Agris, P. F. (1979) Major and Modified Nucleosides in tRNA Hydrolysates by High Performance Liquid Chromatography. *J. Chromatogr.* 173:281-298; Agris, P. F., Tompson, J. G., Gehrke, C. W., Kuo, K. C., and Rice, R. H. (1980) High-Performance Liquid Chromatography and Mass Spectrometry of Transfer RNA Bases for Isotopic Abundance. *J. Chromatogr.* 194:205-212; Gehrke, C. W., Kuo, K. C., McCune, R. A., Gerhardt, K. O., and Agris, P. F. (1981) Quantitative Enzymatic Hydrolysis of tRNAs: RP-HPLC of tRNA Nucleosides. *J. Chromatogr.* 230:297-308; *Chromatography and Modification of Nucleosides* Volumes A, B and C (Gehrke, C. W. and Kuo, K. C. T., eds.), Elsevier Publishing Co. 1990; Agris, P. F. and Sierzputowska-Gracz, H. (1990) Three Dimensional Dynamic Structure of tRNA's by Nuclear Magnetic Resonance. In *Chromatography and Modification of Nucleosides* (Gehrke, C. W. and Kuo, K. C. T., eds.), Elsevier Publishing Co., pp. 225-253; Agris, P. F., Hayden, J., Sierzputowska-Gracz, H., Ditson, S., Degres, J. A., Tempesta, M., Kuo, K. C. and Gehrke, C. W. (1990) Compendium on Biological, Biochemical, Chemical, Physical and Spectroscopic Properties of RNA and DNA Nucleosides. In *Chromatography and Modification of Nucleosides*, Elsevier Publishing Co.

The incomplete removal of the protecting group and lack of a simple assay is a problem for two industries and for numerous researchers world wide: (i) the multitude of companies now providing nucleic acid sequence synthesis products by overnight delivery have difficulty telling their customers the extent to which the product is deprotected; (ii) pharmaceutical companies cannot easily verify for regulatory agencies the purity and/or length of the therapeutic or diagnostic oligonucleotide products they seek to introduce or market. Accordingly, there is a need for simple and reliable techniques for determining the purity and proportion of full length of oligonucleotide products.

SUMMARY OF THE INVENTION

A first aspect of the present invention is an antibody (e.g., a monoclonal or polyclonal antibody) that specifically binds to a synthetic oligomer (i.e., an oligonucleotide or oligopeptide) having a organic protecting group covalently bound thereto, which antibody does not bind to that synthetic oligomer when the organic protecting group is not covalently bound thereto.

A second aspect of the present invention comprises a cell or cells, including cell cultures and isolated cells, that express an antibody as described above. Such cells include hybridoma cells, as well as recombinant cells that contain and express a heterologous nucleic acid encoding the antibody.

A third aspect of the present invention is a method for detecting incomplete deprotection of a synthetic oligomer by immunoassay, said immunoassay comprising the steps of: (a) contacting a synthetic oligomer to an antibody as described above, and then (b) detecting the presence or absence of binding of said antibody to said oligomer, the presence of binding indicating incomplete deprotection of said synthetic oligomer. Any suitable assay format can be employed, including heterogeneous and homogeneous immunoassays. For example, the immunoassay may be an immunoblot-dot assay, or may be a sandwich assay.

A fourth aspect of the present invention is a method for separating protected (including partially and completely protected) synthetic oligomers from fully deprotected synthetic oligomers. The method comprises (a) contacting a mixture of protected from fully deprotected synthetic oligomers to antibodies as described above, wherein the protected synthetic oligomers have the organic protecting group covalently bound thereto, so that the protected synthetic oligomers bind to the antibody; and then separating the antibodies from the fully deprotected oligomers. The antibody may be immobilized on a solid support to facilitate separation. The protected synthetic oligomer may be a partially protected synthetic oligomer (for which one application is the identification and/or purification of full-length versus aborted sequence oligomers) or a fully protected synthetic oligomer that has not undergone deprotection. Any separation format may be used, including but not limited to affinity chromatography.

A fifth aspect of the invention is an article useful for the determining incomplete deprotection of a synthetic oligomer in an immunoassay, said article comprising: (a) a solid support (e.g., a nitrocellulose strip) having a surface portion, said surface portion having at least two separate discrete regions formed thereon; (b) a first oligomer bound to one of said separate discrete regions, said first oligomer having a protecting group bound thereto; and (c) a second oligomer bound to another of said separate discrete regions, said second oligomer not having said protecting group bound thereto; wherein the nucleotide sequence of said first and second oligomers are the same. In a preferred embodiment, the article further comprises (d) a third oligomer bound to another of said separate discrete regions; said third oligomer also having said protecting group bound to said first oligomer bound thereto; wherein said third oligomer is partially deprotected; and wherein the nucleotide sequence of said first, second, and third oligomers are the same.

A sixth aspect of the present invention is a method of making an antibody that specifically binds to a synthetic oligomer having a organic protecting group covalently bound thereto, which antibody does not bind to the said synthetic oligomer when said organic protecting group is not covalently bound thereto, said method comprising the steps of: (a) synthesizing said synthetic oligomer on a solid particulate support (and preferably covalently bound thereto, e.g., with a succinyl linker) with said organic protecting group covalently bound to said synthetic oligomer (or synthesizing a monomer of a single nucleotide on the solid support, with the single nucleotide having said protecting group covalently bound thereto); and then, without removing said oligomer from said solid support; (b) immunizing an animal with said synthetic oligomer bound to said solid support (or monomer bound to said solid support) in an amount sufficient to produce said antibody. Optionally, the solid support can be replaced with a carrier group such as a protein (e.g., bovine serum albumin).

In summary, the antibodies and methods of the present invention are useful in immunoassays, such as for the qualitative and quantitative detection of protecting groups used in organic synthetic processes, with particular application to oligonucleotides or peptides in research, therapeutics, diagnostics and biomedical science. The antibodies of the invention can be used in purification techniques, such as for the separation of final products from by-product contaminants. The instant invention can be used in the course of quality control of oligonucleotide and peptide synthesis, such as in the quality control of drugs for gene therapy, antisense, antigene and control of gene expression, in the quality control of biomedical polymers that may contain protecting groups, and as probes for purification and characterization of synthetic oligomers, particularly oligonucleotides or peptides.

The present invention is explained in greater detail in the drawings herein and the specification set forth below.

DETAILED DESCRIPTION OF THE PREFERRED EMBODIMENTS

Figure 1:
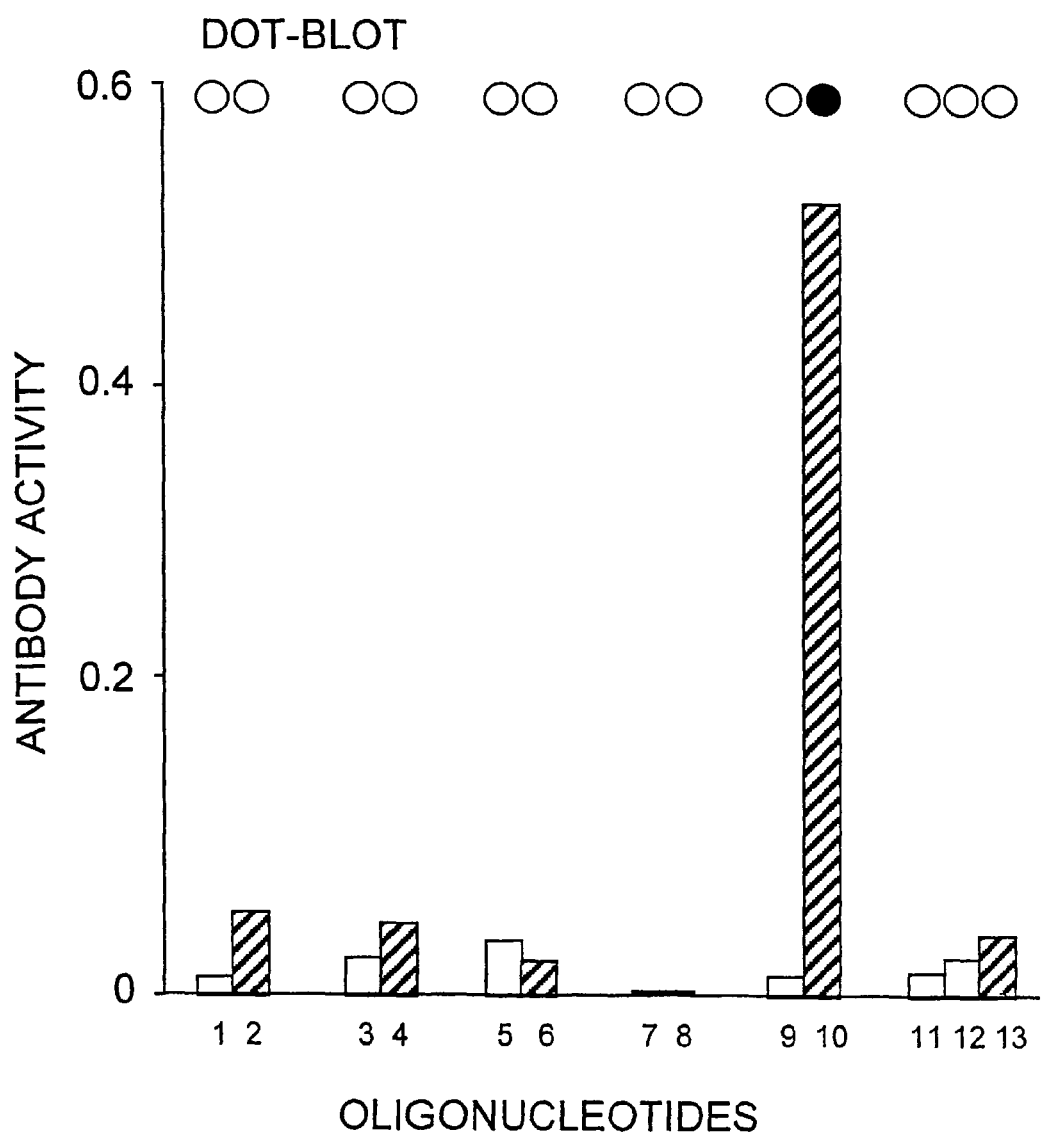
FIG. 1 is a dot-blot immunoassay of monoclonal antibody 1 H11, which selectively binds to oligoIbu-dG20mers.
Figure 2:
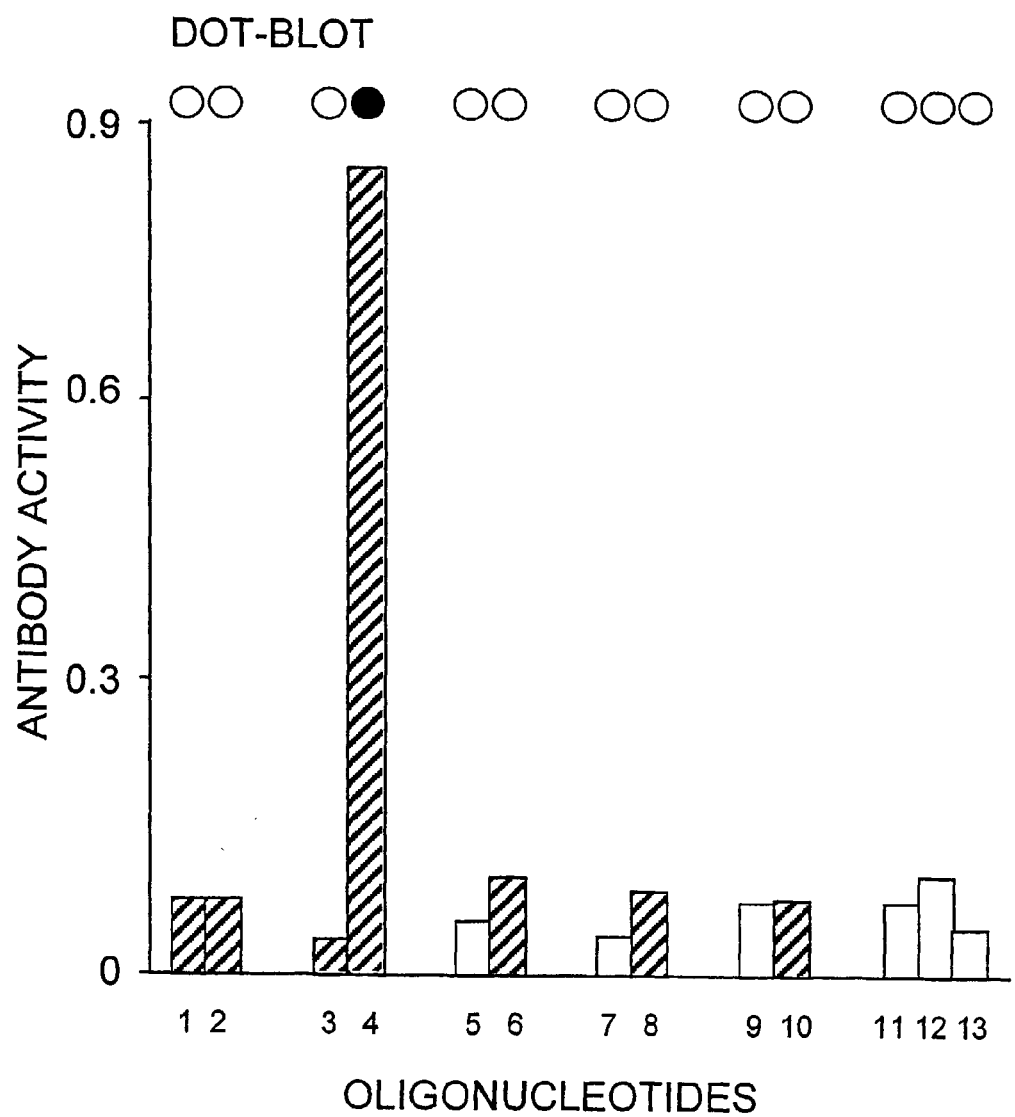
FIG. 2 is a dot-blot immunoassay of monoclonal antibody 7H3, which selectively binds to oligoBz-dC20mers.

1. General Definitions.

"Antibody" as used herein refers to both monoclonal and polyclonal antibodies, refers to antibodies of any immunoglobulin type (including but not limited to IgG and IgM antibodies), and including antibody fragments that retain the hypervariable or binding regions thereof. Antibodies may be of any species of origin, but are typically mammalian (e.g., horse, rat, mouse, rabbit, goat). Antibodies may be bound to or immobilized on solid supports such as nitrocellulose, agarose, glass, organic polymers ("plastics") and the like in accordance with known techniques, and may be labeled with or joined to other detectable groups in accordance with known techniques.

"Binding" as used herein with respect to the selective binding of an antibody to an oligomer has its usual meaning in the art. In general, to obtain useful discrimination in an immunoassay or an affinity purification technique, the antibody should bind to the protected oligomer at an affinity of at least about $k_d=10^{-6}$, $10^{-7}$, or $10^{-8}$ M, and should bind to the unprotected oligomer at an affinity of not greater than about $k_d=10^{-2}$, $10^{-3}$, or $10^{-4}$ M.

"Oligomer" as used herein refers to synthetic oligonucleotides and synthetic oligopeptides, including synthetic oligomers in the naturally occurring form such as DNA and RNA, and modified backbone chemistries as discussed below. Oligonucleotides are currently preferred in carrying out the present invention, and the instant invention is primarily explained with reference to oligonucleotides herein. However, the methods and techniques described herein may also be applied to oligopeptides, oligosaccharides, etc. (i.e., any synthetically produced polymer requiring protecting groups for synthesis).

"Nucleotide" as used herein refers to a subunit of an oligonucleotide comprising a pentose, a nitrogenous heterocyclic base (typically bound to the 1 position of the pentose), and a phosphate or phosphoric acid group (typically bound at the 5' position of the pentose) but absent, or considered bound at the 3' position, in the 5' terminal nucleotide of an oligonucleotide. These structures are well known. See, e.g., A. Lehninger, *Biochemistry*, 309-320). "Nucleoside" typically refers to a nucleotide, absent a phosphoric acid or phosphate group.

"Protecting group" as used herein has its conventional meaning in the art and refers to a chemical moiety, group or substituent that is coupled, typically covalently coupled, to an atom in a molecule prior to a chemical reaction involving that molecule (typically in an organic synthesis), so that the chemical reaction is averted at the atom to which the protecting group is coupled. Typically, the protecting group is then chemically removed from the intermediate molecule for preparation of the final product, although removal techniques may not be entirely successful leading to only partial deprotection of the final product (i.e., the presence of at least one protecting group remaining on that molecule). Protecting groups may be intentionally left on a molecule for purposes of generating or testing an antibody as described herein.

"Deprotection" or "deprotected" as used herein refers to the absence of protecting groups employed during chemical oligonucleotide synthesis from a molecule. Such protecting groups are described below. The presence of such a protecting group may indicate insufficient elongation of the oligonucleotide, when the protecting group is chain terminating. Chemically synthesized oligonucleotides are ideally fully deprotected, but the present invention is employed to detect partial or incomplete deprotection of such oligonucleotides (that is, the presence of at least one protecting group as described below in the oligonucleotide).

"Base" as used herein with respect to oligonucleotides refers to a nitrogenous heterocyclic base which is a derivative of either purine (e.g., adenine, guanine) or pyrimidine (e.g., uracil, thymine, cytosine). Pyrimidine bases are bound to the pentose by the 1 ring nitrogen; Purine bases are bonded to the pentose by the 9 ring nitrogen. Preferred bases are those that contain a free amino group, such as guanine, adenine, and cytosine (the protecting group is then covalently bound to the free amino group by substitution of one, or both, of the hydrogens on the free amino group). However, the present invention may be used with any purine or pyrimidine base, whether standard or modified/rare, that contains a free amino group for protection, or other group requiring protection during synthesis thereof in an oligonucleotide. Examples of standard and modified/rare bases are those found in the nucleosides set forth in Table 1 below.

TABLE 1

Standard and modified nucleosides and their standard abbreviations.

| abbreviation | base |
| --- | --- |
| U | uridine |
| C | cytidine |
| A | adenosine |
| G | guanosine |
| T | thymidine |
| ?A | unknown modified adenosine |
| m1A | 1-methyladenosine |
| m2A | 2-methyladenosine |
| i6A | $N^6$-isopentenyladenosine |
| ms2i6A | 2-methylthio-$N^6$-isopentenyladenosine |
| m6A | $N^6$-methyladenosine |
| t6A | $N^6$-threonylcarbamoyladenosine |
| m6t6A | $N^6$-methyl-$N^6$-threonylcarbonyladenosine |
| ms2t6A | 2-methylthio-$N^6$-threonylcarbamoyladenosine |
| Am | 2'-O-methyladenosine |
| I | Inosine |
| m1I | 1-methylinosine |
| Ar(p) | 2'-O-(5-phospho)ribosyladenosine |
| io6A | $N^6$-(cis-hydroxyisopentenyl)adenosine |
| ?C | Unknown modified cytidine |
| s2C | 2-thiocytidine |
| Cm | 2'-O-methylcytidine |
| ac4C | $N^4$-acetylcytidine |
| m5C | 5-methylcytidine |
| m3C | 3-methylcytidine |
| k2C | lysidine |
| f5C | 5-formylcytidine |
| f5Cm | 2'-O-methyl-5-formylcytidine |
| ?G | unknown modified guanosine |
| Gr(p) | 2'-O-(5-phospho)ribosylguanosine |
| m1G | 1-methylguanosine |
| m2G | $N^2$-methylguanosine |
| Gm | 2'-O-methylguanosine |
| m22G | $N^2N^2$-dimethylguanosine |
| m22Gm | $N^2,N^2,2'$-O-trimethylguanosine |
| m7G | 7-methylguanosine |
| fa7d7G | archaeosine |
| Q | queuosine |
| manQ | mannosyl-queuosine |
| galQ | galactosyl-queuosine |
| Yw | wybutosine |
| o2yW | peroxywybutosine |
| ?U | unknown modified uridine |
| mnm5U | 5-methylaminomethyluridine |
| s2U | 2-thiouridine |
| Um | 2'-O-methyluridine |
| s4U | 4-thiouridine |
| ncm5U | 5-carbamoylmethyluridine |
| mcm5U | 5-methoxycarbonylmethyluridine |
| mnm5s2U | 5-methylaminomethyl-2-thiouridine |
| mcm5s2U | 5-methoxycarbonylmethyl-2-thiouridine |
| cmo5U | uridine 5-oxyacetic acid |
| mo5U | 5-methoxyuridine |
| cmnm5U | 5-carboxymethylaminomethyluridine |
| cmnm5s2U | 5-carboxymethylaminomethyl-2-thiouridine |
| acp3U | 3-(3-amino-3-carboxypropyl)uridine |
| mchm5U | 5-(carboxyhydroxymethyl)uridinemethyl ester |
| cmnm5Um | 5-carboxymethylaminomethyl-2'-O-methyluridine |
| ncm5Um | 5-carbamoylmethyl-2'-O-methyluridine |
| D | Dihydrouridine |
| ψ | pseudouridine |
| m1ψ | 1-methylpseudouridine |

TABLE 1-continued

Standard and modified nucleosides and their standard abbreviations.

| abbreviation | base |
|---|---|
| ψm | 2'-O-methylpseudouridine |
| m5U | ribosylthymine |
| m5s2U | 5-methyl-2-thiouridine |
| m5Um | 5,2'-O-dimethyluridine |

See Sprinzl et al., *Nucleic Acids Res.* 26, 148 (1998).

Applicants specifically intend that the disclosures of all United States patent references cited herein be incorporated by reference herein in their entirety.

2. Protecting Groups.

The particular protecting group will depend upon the oligomer being synthesized and the methodology by which that oligomer is synthesized.

For the synthesis of oligonucleotides, suitable protecting groups include alkyl, aryl, alkylaryl, arylalkyl groups, which may contain one or more hetero atoms such as N, O, or S, and which may be substituted or unsubstituted (e.g., a carbonyl group). Examples of protecting groups include, but are not limited to, the following: acetyl; isobutyryl; 2-(t-butyldiphenyl-silyloxymethyl)benzoyl; naphthalol; iso-butyryloxycarbonyl; levulinyl; fluorenylmethoxycarbonyl; 2-nitrothiophenol; 2,2,2-trichloro-t-butoxycarbonyl, ethoxycarbonyl; benzyloxycarbonyl; p-nitrophenyl-ethyloxycarbonyl; N'N-dimethylformamidine; formyl; benzoyl, toluyl; 2,4-6-trimethylbenzoyl; anisoyl; 2,4-dimethylphenyl; 2,4,6-trimethylphenyl; triphenylthiomethyl; pivoloiloxymethyl; t-butoxycarbonyl; p-nitrophenylethyl; methoxyethoxymethyl; butylthiocarbonyl; 2-methyl-pyridine-5-yl; 2-nitrothiophenol; 2,4-dinitrothiophenyl; 2-nitro-4-methylthiophenyl; p-nitrophenylsulphonylethyl; 5-chloro-8-hydroxyquinoline; thiophenyl; β-cyanoethyl; phenylethyl; p-nitrophenylethyl; pyridylethyl; 2-N-methylimidazolylphenyl; methyl; allyl; trichloroethyl; dibenzoyl; p-nitrophenylethoxycarbonyl; benzoyl and substituted derivatives thereof; 2(acetoxymethyl) benzoyl; 4,4',4"-tris-(benzyloxy) trityl; 5-methylpyridino-2-yl; phenylthioethyl; diphenylcarbamoyl; 3,4-dimethoxybenzyl; 3-chlorophenyl; 2-nitrophenyl; 9-phenylxanthen-9-yl; 9-(p-methoxyphenyl)xanthen-9-yl; 9-(p-octadecyloxyphenyl)xanthen-9-yl; "bridged" bis-dimethoxytrityl groups; phthaloyl; succinyl; benzensulphonylethoxycarbonyl; 4,4',4"-tris(bevulinyloxy) trityl; p-phenylazophenyloxycarbonyl; o-substituted benzoyl; 4,4',4"-tris-(4,5-dichlorophalimidin)trityl; levelinyl; alkyloxy and aryloxyacetyl; 1,3-benzodithiol-2-yl; tetrahydrofuranyl; [2-(methylthio)phenyl]thiomethyl; 1-(2-chloroethoxy)ethyl; 1-[(2-fluoro-phenyl]4-methoxy piperidin-4-yl; 4-methoxytetrahydropyran-4-yl; (1-methyl-1-methoxy) ethyl; tetrahydropyranyl; 3-methoxy-1,5-dicarbomethoxy-pentam-3-yl; 2-nitrobenzyl; benzyl; 4-nitrophenylethyl-sulphonyl; t-butyldimethylsilyl; 4-methoxybenzyl; 3,4-dimethoxybenzyl; 9-p-methoxyphenylthioxanthen-9-yl; compounds of the formula $R_1R_2R_3C$—, wherein $R_1$, $R_2$, and $R_3$ are each independently selected from the group consisting of phenyl, p-monomethoxyphenyl, o-monomethoxphenyl, biphenyl, p-fluorophenyl, p-chlorophenyl, p-methylphenyl, p-nitrophenyl, etc.

3. Oligonucleotides.

Synthetic oligonucleotides that contain protecting groups and may be used to carry out the present invention include both the naturally occurring forms such as DNA and RNA, and those with modified backbone chemistries, such as poly (phosphate derivatives) such as phosphonates, phosphoramides, phosphonamides, phosphites, phosphinamides, etc., poly (sulfur derivatives) e.g., sulfones, sulfonates, sulfites, sulfonamides, sulfenamides, etc. It will be noted that antibodies of the invention may be characterized by their selective binding to particular "reagent" or "benchmark" oligonucleotides, but the same antibodies may also bind to a variety of other oligonucleotides (e.g., longer nucleotides) or other compounds that contain the same protecting group.

For example, an oligonucleotide to which the antibody selectively binds may consist of from 3 to 20 nucleotides, and wherein one of said nucleotides is a protected nucleotide according to Formula (I) below:

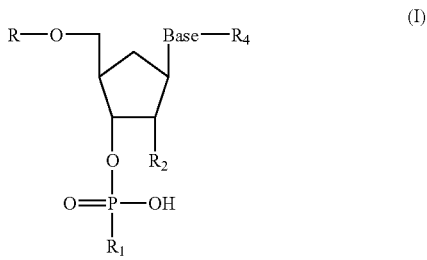

(I)

wherein:

R is H or a protecting group, such as dimethoxytrityl; subject to the proviso that R is a covalent bond to an adjacent nucleotide when said protected base is not a 5' terminal nucleotide in said oligonucleotide;

$R_1$ is H or a protecting group such as β-cyanoethyl; subject to the proviso that $R_1$ is a covalent bond to an adjacent nucleotide when said protected base is not a 3' terminal nucleotide in said oligonucleotide;

$R_2$ is H or —$OR_3$;

$R_3$ is H or a protecting group such as tert-butyldimethylsilyl;

Base is a purine or pyrimidine base; and $R_4$ is a protecting group bonded to an amino group of said base, such as a protecting group is selected from the group consisting of acetyl (Ac), benzoyl (Bz), dimethylformamidine (dmf), isobutyryl (Ibu), phenoxyacetyl (Pac), and isopropyl-phenoxyacetyl (Ipr-pac);

and further subject to the proviso that when one of R, $R_1$, $R_3$ and $R_4$ is a protecting group, then the others of R, $R_1$, $R_3$ and $R_4$ are not protecting groups.

In one particular embodiment of the foregoing, the antibody may be one that selectively binds to an oligonucleotide that consists of from 3 to 20 nucleotides and has a 5' nucleotide, and wherein said 5' nucleotide is a protected nucleotide according to Formula (I):

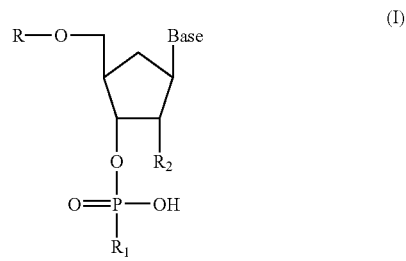

(I)

wherein:

R is a protecting group such as dimethoxytrityl;

$R_1$ is a covalent bond to an adjacent nucleotide;

$R_2$ is —H or —OH; and

Base is a purine or pyrimidine base.

In another particular embodiment of the foregoing, the antibody may be one that selectively binds to an oligonucleotide that consists of from 3 to 20 nucleotides and has a 3' nucleotide, and wherein said 3' nucleotide is a protected nucleotide according to Formula (I):

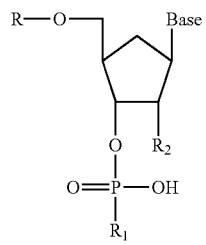

(I)

wherein:
R is a covalent bond to an adjacent nucleotide;
$R_1$ is a protecting group such as β-cyanoethyl;
$R_2$ is H or —OH; and
Base is a purine or pyrimidine base.

In another particular embodiment of the foregoing, the antibody may be one that selectively binds to an oligonucleotide that consists of from 3 to 20 nucleotides, and wherein one of said nucleotides is a protected nucleotide according to Formula (I):

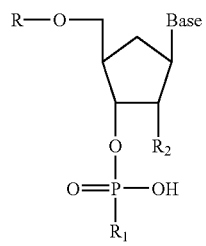

(I)

wherein:
R is a covalent bond to an adjacent nucleotide;
$R_1$ is a covalent bond to an adjacent nucleotide;
$R_2$ is —$OR_3$;
$R_3$ a protecting group such as tert-butyldimethylsilyl; and
Base is a purine or pyrimidine base.

In still another particular embodiment of the foregoing, the antibody may be one that selectively binds to an oligonucleotide that consists of from 3 to 20 nucleotides, and wherein one of said nucleotides is a protected nucleotide according to Formula (I):

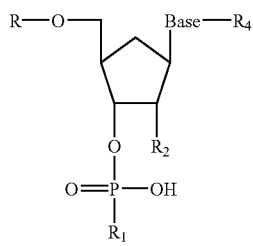

(I)

wherein:
R is a covalent bond to an adjacent nucleotide;
$R_1$ is a covalent bond to an adjacent nucleotide;
$R_2$H or —OH;
Base is a purine or pyrimidine base; and
$R_4$ is a protecting group bonded to an amino group of said base, such as acetyl, benzoyl, dimethylformamidine, isobutyryl, phenoxyacetyl, and isopropyl-phenoxyacetyl.

Thus, examples of protected bases that may be employed in the structures shown above include, but are not limited to, adenine, guanine, and cytosine, as follows:

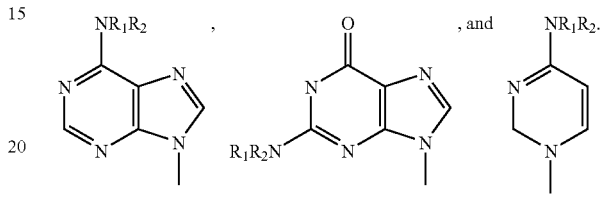

wherein $R_1$ and $R_2$ are both H in an unprotected base, and either $R_1$ or $R_2$ are a protecting group as described above (e.g. Pac, Ipr-pac, Ibu, Bz, Ac, dmf) for a protected base. Likewise, modified nucleosides have protecting groups at the modifications that are chemically reactive.

In one embodiment of the invention, the oligonucleotides are peptide nucleic acids, and the protecting groups are those protecting groups employed in the synthesis of peptide nucleic acids, including but not limited to those described in U.S. Pat. No. 6,133,444.

In still another particular embodiment of the foregoing, the antibody may be one that selectively binds to an oligonucleotide that consists of from 3 to 20 nucleotides, and wherein one of said nucleotides is a protected with a photolabile protecting group, including but not limited to those described in U.S. Pat. Nos. 5,744,101 and 5,489,678 (assigned to Affymax).

4. Antibodies.

As noted above, the present invention provides antibodies (e.g., a monoclonal or polyclonal antibody) that specifically bind to a synthetic oligonucleotide having a organic protecting group covalently bound thereto, which antibody does not bind to said synthetic oligonucleotide when said organic protecting group is not covalently bound thereto.

The antibody may be provided immobilized on (or bound to) a solid support in accordance with known techniques, or may be provided in a free, unbound form (e.g., lyophilized, frozen, in an aqueous carrier, etc.). Whether or not an antibody is immobilized will depend upon the particular immunoassay or affinity purification technique in which the antibody is used, and is determined by the known parameters for such techniques. Similarly, the antibody may be bound to or conjugated with suitable detectable groups, such as an enzyme (e.g., horseradish peroxidase), a member of a binding pair such as biotin or avidin, a radioactive group or a fluorescent group such as green fluorescent protein, also in accordance with known techniques, typically depending upon the immunoassay format in which the antibody is used.

5. Immunoassay Methods.

The present invention provides a method for detecting incomplete deprotection of a synthetic oligonucleotide (including aborted sequences that still contain a protecting group) by immunoassay. In general, such an immunoassay comprises the steps of: (a) contacting a synthetic oligonucleotide to an antibody as described above, and then (b) detecting the presence or absence of binding of said antibody to said oligonucleotide, the presence of binding indicating incomplete deprotection of said synthetic oligonucleotide. Any suitable assay format can be employed, including heterogeneous and homogeneous immunoassays. For example, the immunoassay may be an immunoblot-dot assay, or may be a sandwich assay. The oligonucleotides being tested for deprotection may be in any suitable form, such as in solution or immobilized on a solid support.

Figure 10:
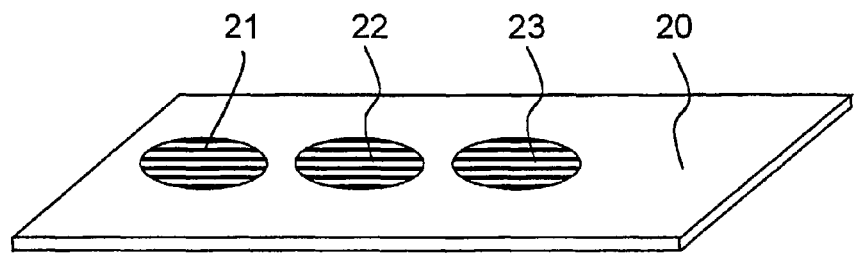
FIG. 10 shows a substrate carrying different oligonucleotides of the same sequence, but with varying degrees of deprotection, that may be used as a testing standard to screen similar oligonucleotides of the same sequence for varying degrees of protection or deprotection.

In a preferred embodiment, the detection method employs a "dip stick" or the like, in which binding of the antibody to the test oligonucleotide is compared to binding of the antibody to a set of known oligonucleotides, all immobilized on a common solid support. Such an article, as illustrated in FIG. 10, useful for determining incomplete deprotection of a synthetic oligonucleotide in an immunoassay, comprises: (a) a solid support (e.g., a nitrocellulose strip) 25 having a surface portion, said surface portion having at least two separate discrete regions 26, 27 formed thereon; (b) a first oligonucleotide bound to one of said separate discrete regions, said first oligonucleotide having a protecting group bound thereto (e.g., at least one protecting group); and (c) a second oligonucleotide bound to another of said separate discrete regions, said second oligonucleotide not having said protecting group bound thereto; wherein the nucleotide sequence of said first and second oligonucleotides are the same. In a preferred embodiment, the article further comprises (d) a third oligonucleotide bound to another of said separate discrete regions 28; said third oligonucleotide also having said protecting group bound to said first oligonucleotide bound thereto; wherein said third oligonucleotide is partially deprotected (i.e., has a number of protecting groups covalently bound thereto which is intermediate between that bound to the first and second oligonucleotide, e.g., at least one, two three or four more protecting groups than the first oligonucleotide, up to at least 10, 20 or more protecting groups than the first oligonucleotide); and wherein the nucleotide sequence of said first, second, and third oligonucleotides are the same. Of course, still more oligonucleotides carrying varying numbers of protecting groups may be included on the substrate in additional separate and discrete locations, if desired. The discrete regions to which the separate oligonucleotides are bound may be in any form, such as dots.

6. Affinity Purification Methods.

In addition to immunoassays, the present invention also provides affinity purification techniques for the separation of fully deprotected oligonucleotides from partially deprotected (including fully protected) oligonucleotides (e.g., both oligonucleotides that have been subjected to a deprotection process to remove the protecting group, and oligonucleotides that have not). Such a procedure typically comprises (a) contacting a mixture of protected and fully deprotected synthetic oligonucleotides to antibodies as described above, wherein the protected synthetic oligonucleotides have the organic protecting group for which the antibody is selective covalently bound thereto, so that the protected synthetic oligonucleotides bind to the antibody; and then separating said antibodies from said fully deprotected oligonucleotides. The antibody may be immobilized on a solid support to facilitate separation. The protected synthetic oligonucleotide may be a partially protected synthetic oligonucleotide, or a fully protected synthetic oligonucleotide that has not undergone deprotection. Any separation format may be used, including but not limited to affinity chromatography.

7. Production of Antibodies.

A method of making an antibody that specifically binds to a synthetic oligonucleotide having a organic protecting group covalently bound thereto, which antibody does not bind to the said synthetic oligonucleotide when said organic protecting group is not covalently bound thereto, comprises the steps of: (a) synthesizing the synthetic oligonucleotide on a solid particulate support (and preferably covalently bound thereto, e.g., with a succinyl linker) with the organic protecting group covalently bound to said synthetic oligonucleotide; and then, without removing the oligonucleotide from said solid support; and (b) immunizing an animal with the synthetic oligonucleotide bound to the solid support in an amount sufficient to produce the antibody. In addition, a single nucleotide can be bound to the solid particulate support with the organic protecting group bound thereto, and used as described hereinabove.

The synthesis step may be carried out on the solid support in accordance with known techniques. The solid support may be in particulate form prior to synthesis, or may be fragmented into particles after synthesis. In general, the solid supports are beads, which may be completely solid throughout, porous, deformable or hard. The beads will generally be at least 10, 20 or 50 to 250, 500, or 2000 μm in diameter, and are most typically 500 to 250 μm in diameter. Any convenient composition can be used for the solid support, including cellulose, pore-glass, silica gel, polystyrene beads such as polystyrene beads cross-linked with divinylbenzene, grafted copolymer beads such as polyethyleneglycol/polystyrene, polyacrylamide beads, latex beads, dimethylacrylamide beads, composites such as glass particles coated with a hydrophobic polymer such as cross-linked polystyrene or a fluorinated ethylene polymer to which is grafted linear polystyrene, and the like. Where separate discrete solid supports such as particles or beads are employed, they generally comprise from about 1 to 99 percent by weight of the total reaction mixture.

In a preferred embodiment, the synthesizing step is followed by the step of fragmenting the solid support (e.g., by crushing) prior to the immunizing step. Polyclonal antibodies may be collected from the serum of the animal in accordance with known techniques, or spleen cells may be collected from the animal, a plurality of hybridoma cell lines produced from the spleen cells; and then a particular hybridoma cell line that produces the antibody isolated from the plurality of hybridoma cell lines.

A particular protocol for the production of antiserum/polyclonal antibodies and monoclonal antibodies against protecting groups used in nucleic acid and other synthesis typically involves the following steps: (a) preparation of oligonucleotides and others that contain or do not contain protecting groups; (b) immunization of animals with those preparations; (c) screening of animals to identify those that exhibit antibodies against protecting groups; (d) production of monoclonal antibody by classical fusion method; (e) optionally, production of scFab, Fab fragments and whole antibody molecules by antibody engineering; and (f) evaluation and characterization of monoclonal antibodies against the protecting groups. Each of these steps is discussed in greater detail below.

Synthetic oligonucleotides that contain protecting groups can be synthesized in a variety of ways known to those skilled in the art. For example, protecting groups can be attached to individual nucleotides that are linked to controlled pore glass (CPG) beads. An example is:

CPG bead—dT (only with DMT group).

In the alternative, protecting groups may be attached to oligonucleotide chains that are linked to CPG beads. Examples include:

Pac-dA—Pac-dA—CPG beads with Bz-dC and Ibu-dG;
Ipr-Pac-dG—Ipr-Pac-dG—CPG beads with Bz-dC and Ibu-dG;
Ac-dC—Ac-dC—CPG beads with Bz-dC and Ibu-dG;
dmf-G—dmf-G—CPG beads with Bz-dC and Ibu-dG; and
mixtures of the four oligonucleotides described above.

In another alternative, protecting groups may be attached to oligonucleotide chains that are partially deprotected (the procedure for deprotection will be described bellow). Examples include:

Poly dT20mers (only with DMT group);
Poly dT20mers (only with cyanoethyl groups);
Poly Ibu-dg 20mers (partially deprotected);
Poly Ipr-Pac-dG 20mers (partially deprotected);
Poly Bz-dC 20mers (partially deprotected);
Poly Pac-dA 20mers (partially deprotected); and
Poly Ac-dC 20mers (partially deprotected).

Synthetic oligonucleotides prepared as described herein may be partially deprotected as follows: (a) add 30% ammonium hydroxide solution to synthetic polynucleotides, then incubate at room temperature for different time periods (5, 10 and 30 min); (b) take the ammonium solution of treated oligomers and add into 1:1 diluted acetic acid pre-cooled at 4° C. and according to 1:4 ratio of ammonium to acetic acid; (c) keep samples in ice bath for 30 min; (d) dry samples with speed-Vac; (e) dissolve the dried pellets in water; (f) desalt samples with Sephadex G-25 column; (g) dry samples with speed-Vac; and (h) dissolve the desalted samples in water.

Synthetic oligonucleotides prepared as described herein may be completely deprotected by any suitable technique. One particular technique is as follows: (a) add 30% ammonium hydroxide solution to synthetic oligonucleotides, then incubate at 65° C. for 6 hrs; (b) dry samples with speed-Vac; (c) dissolve the dried pellets in water; (d) desalt samples with Sephadex G-25 column; and (e) dry samples with speed-Vac; (f) redissolve desalted samples in water.

Partially and completely deprotected oligonucleotides may be characterized for further use or to verify procedures by any suitable means, including but not limited to gel electrophoresis, urea-acrylamide gel electrophoresis, 5'end labeling with T4 polynucleotide kinase, HPLC analysis, mass spectrometry, etc.

Suitable animals can be immunized with the oligonucleotides described above by parenteral injection of the oligonucleotide in a suitable carrier, such as sterile saline solution. Injection may be by any suitable route, including but not limited to subcutaneous, intraperitoneal, intravenous, intraarterial, intramuscular, etc. Suitable animals are typically mammals, including mice, rabbits, rats, etc.

In a particular embodiment, for the production of monoclonal antibodies, young female BALB/c mice are used, and the time course of injection of the antigen material is:

| | |
|---|---|
| first day | initial injection |
| 14th day | first boosting |
| 28th day | second boosting |
| 4 day before fusion | final boosting |

Additional injections may be employed if desired. The antigen amount may be 50 µg or 100 µg of oligonucleotides unprotected (for control antibody) or protected, for each mouse per time. When, as preferred, beads or other solid support used as the support for oligonucleotide synthesis are injected into the animal, the beads or particles are suspended in water, then injected into mice. If a nucleotide solution is used, then the solution is mixed with complete or incomplete Freund's adjuvant and injected into mice.

Polyclonal antibodies can be harvested from animals immunized or innoculated as described above in accordance with known techniques, or spleen cells harvested from the animals, hybridoma cell lines produced from the spleen cells, and the hybridoma cell lines screened for the production of desired antibodies, also in accordance with known techniques.

Oligonucleotides that contain or do not contain biotin molecules at 3' or 5' ends (for ELISA assay as described below) may be synthesized in accordance with standard techniques. Examples are:

Poly Ibu-dG 20 mers (with or without biotin);
Poly Ibu-dA 20 mers (with or without biotin);
Poly Ibu-dC 20 mers (with or without biotin);
Poly Ipr-Pac-dG 20 mers (with or without biotin);
Poly Bz-dC 20 mers (with or without biotin);
Poly Bz-dA 20 mers (with or without biotin);
Poly dT 20 mers (with or without biotin);
Poly Pac-dA 20 mers (with or without biotin);
Poly Ac-dC 20 mers (with or without biotin); and
Poly dmf-G 20 mers (with or without biotin).

Antibodies produced as described above may be characterized by any suitable technique to determine the binding properties thereof, including but not limited to Western blot and immunodot-blot.

In addition to the use of polyclonal and monoclonal antibodies, the present invention contemplates the production of antibodies by recombinant DNA, or "antibody engineering" techniques. For example, mRNA isolated from hybridoma cells may be used to construct a cDNA library and the sequence encoding whole antibody or antibody fragments (e.g., scFab or Fab fragments) isolated and inserted into suitable expression vector, and the expression vector inserted into a host cell in which the isolated cDNA encoding the antibody is expressed.

Monoclonal Fab fragments may be produced in *Escherichia coli* by recombinant techniques known to those skilled in the art. See, e.g., W. Huse, *Science* 246, 1275-81 (1989).

8. Screening of Antibodies.

Screening sera and hybridoma cell culture media for protecting group specific antibodies may be carried out as follows:

A. Sera
1. Pre-immune (prior to immunization) sera are collected by standard means from the mice to be inoculated with protecting group conjugated to a solid support (directly or through an oligomer).
2. Post-inoculation sera are also collected
3. An ELISA assay is performed in which the specific protecting group remains on a biotinylated oligonucleotide conjugated to the microtiter plate. Other microtiter plate wells contain control oligomers that have no protecting groups, or oligonucleotides with other protecting groups. The secondary antibody is a goat anti-mouse IgG with a conjugated phosphotase for visualization of antibody
4. Those mice that have positive activity against the specific protecting group are boosted and sacrificed for the production of hybridomas.

B. Hybridoma Cell Culture Media
1. Approximately 1000 cultures are generated from each spleen hybrid cell production.
2. Cultures are grown in microtiter plate wells, 96 well plates.

3. Culture medium is removed from each well and used in ELISA assays as described above in which each of the ~1000 microtiter plate wells contain the protected oligonucleotide conjugated to the plate.
4. Those cultures producing antibody that has positive activity are transferred to larger culture wells, 24 well microtiter plates.
5. Culture media from the larger cultures are re-tested for activity against the protecting group and are also assayed for specificity; i.e. controls of no protecting group and of other protecting groups.
6. Those cultures that are positive are cloned out (diluted), re-tested and cloned out again to the point that each final culture must be the result of one cell; i.e. mono-culture. Media from these final cultures are thoroughly assessed for specificity and affinity. Specificity and affinity are assessed using a dot-blot assay.

C. Dot-Blot Assays in lieu of ELISA Assays

1. Antibodies against some protecting groups are not tractable to being tested in the microtiter plate well environment and must be tested using a dot-blot assay. One example is the 5'-terminal protecting group, dimethyltrityl (DMT).
2. The Dot-blot assay on a nitrocellulose membrane is accomplished as described elsewhere in the application for most purposes. However, this is not possible in assessing antibody production by ~1000 microtiter well cultures with little media available. Thus, a novel adaptation has been developed.
    a) The protected oligonucleotide is attached in dots to the nitrocellulose using UV-crosslinking. With DMT, the presence of the 5'-DMT on the membrane is confirmed by treatment of a dot with mild acid—the dot turns yellow-orange. The presence of the 3'-biotin can be confirmed with a commercial avidin stain.
    b) The membrane is blocked (see dot-blot assay).
    b) The dry membrane dots are carefully marked (pencil) and "punched" out of the membrane.
    c) Individual dots are added to the cell culture media in individual microtiter plate wells and incubated.
    d) The individual dots are removed and passed on through the washing, secondary antibody, phosphotase reaction and color development using microtiter plate wells with the appropriate reagents.
    e) Those dots that are positive are related back to the original microtiter plate well cultures from which the small amount of culture media was obtained.
    f) Further culturing and cloning is accomplished as described in B.
9. Testing of Microarrays.

The present invention may be used to test or screen oligonucleotides that are immobilized on a solid support such as a microarray for insufficient deprotection or elongation of the oligonucleotides synthesized thereon.

Solid supports used to carry out the present invention are typically discrete solid supports. Discrete solid supports may be physically separate from one another, or may be discrete regions on a surface portion of a unitary substrate. Such "chip-type" or "pin-type" solid supports are known. See, e.g., U.S. Pat. Nos. 5,143,854 to Pirrung; 5,288,514 to Ellman (pin-based support); 5,510,270 to Fodor et al. (chip-based support). Additional non-limiting examples of oligonucleotide arrays which may be used to carry out the present invention, and methods of making the same, include but are not limited to those described in U.S. Pat. Nos. 5,631,734; 5,599,695; 5,593,839; 5,578,832; 5,510,270; 5,571,639; 6,056,926; 5,445,934; and 5,703,223. Such devices may be used as described therein to carry out the instant invention.

The solid support or substrate from which the array is formed may be comprised of any suitable material, including silicon. The oligonucleotides may be polymerized or grown in situ from monomers (or individual nucleotides) in situ on the microarray (in which case none of the currently available techniques for detecting protecting groups would be useful for detecting incomplete deprotection or elongation of the oligonucleotides on the array, as one cannot pass the solid support through an analytical device) or the oligonucleotides may be polymerized separately and then linked to the appropriate regions of the solid support. The array may include any number of different oligonucleotides in different separate and discrete regions thereon, examples including arrays of at least 1,000, at least 2,000, at least 10,000, or at least 20,000 different oligonucleotides in different separate and discrete regions.

In general, a method of screening an oligonucleotide array for insufficient deprotection or insufficient elongation of oligonucleotides therein comprises the steps of:
(a) providing an oligonucleotide array as described above;
(b) providing an antibody as described above (that is, an antibody that specifically binds to a synthetic oligonucleotide having an organic protecting group covalently bound thereto, which antibody does not bind to said synthetic oligonucleotide when said organic protecting group is not covalently bound thereto). Preferably the antibody is one that specifically binds to an oligonucleotide having a protecting group, where the protecting group was employed in the course of the organic synthesis of oligonucleotides carried by that array. Then;
(c) contacting said oligonucleotide array to said antibody to thereby detect the presence of insufficient deprotection or insufficient elongation of oligonucleotides therein. Such detection, which may be qualitative or quantitative, may be carried out by any suitable immunoassay technique as described above.

In the method, steps (b) to (c) may be repeated at least once, with a different antibody on each repetition, so that a plurality of different protecting groups which may be present on oligonucleotides in the array may be detected.

Preferably, once insufficient deprotection (the presence of protecting groups) in oligonucleotides in one or more (e.g., plurality) of the separate and discrete regions is detected, the method further comprises generating a record or indicia recording the presence of insufficient deprotection or insufficient elongation of oligonucleotides in the least one separate and discrete location (or plurality of separate and discrete locations) on the array. The indicia may be a qualitative or quantitative indicia of insufficient deprotection (including insufficient elongation).

Figure 11:
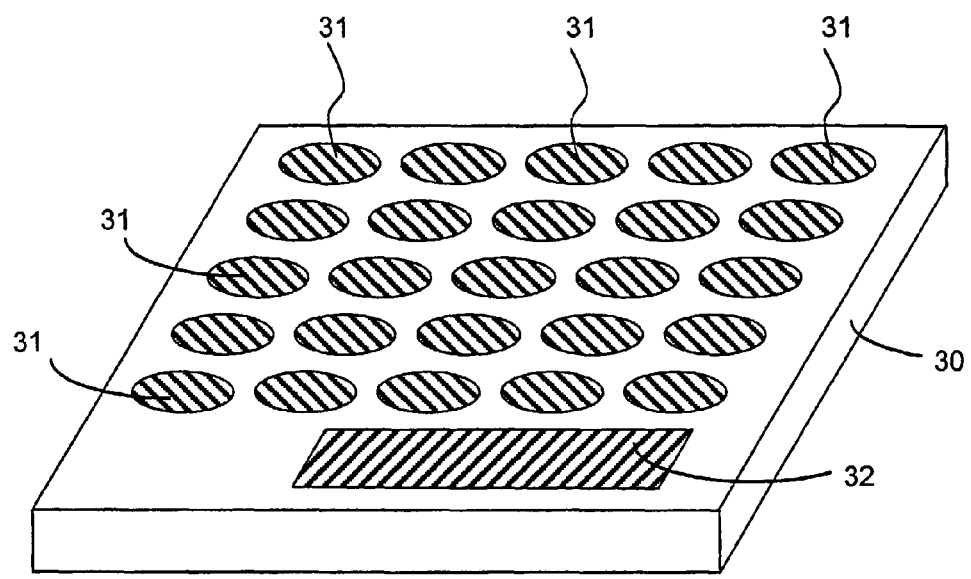
FIG. 11 illustrates an oligonucleotide array that may be screened for the presence of protecting groups or insufficient elongation with antibodies of the present invention.

The foregoing methods provide a correctable oligonucleotide array as illustrated in FIG. 11. The array comprises, in combination:
(a) a substrate 30 having a plurality of different oligonucleotides immobilized thereon, with the different oligonucleotides immobilized in different separate and discrete locations 31 on said substrate; and
(b) a plurality of indicia associated with said array, these indicia recording the presence of insufficient deprotection or insufficient elongation of a plurality of different oligonucleotides, said different oligonucleotides located in separate and discrete locations on said array. These indicia may be printed in a region of the array 32 by a technique such a microlithography, printed on conventional medium such as paper and shipped with the array, stored in a memory or memory device connected to or formed on the array chip (which may be incorporated at location 32), provided in a separate data or computer file which may be provided on a computer-readable medium such as a floppy diskette or CD-ROM, stored on a web site on the world wide web for downloading by the end user of the array, etc. When the indicia are provided in a separate data file, the array preferably further includes an identifier such as a code number formed on, connected to or associated with the array (e.g., printed on a package containing the array, or on an information sheet packaged with the array, and/or printed directly on the array). The identifier may then be associated with the separate indicia (e.g., printed on a data sheet, used as a pass-word, file identifier and/or access code for the computer file, etc.) to insure the correct indicia containing the record of insufficient deprotection and/or elongation are ultimately associated with the array by the ultimate end user of the array.

A data device or memory device connected to the array may be carried out in accordance with known techniques, as described in U.S. Pat. Nos. 5,925,562; 6,017,496; 5,751,629; and 5,741,462, and such devices used as described therein to carry out the instant invention.

The end user of the array may utilize the indicia described above to compensate for insufficient deprotection or insufficient elongation of oligonucleotides on said array in a method comprising:
 (a) providing a substrate as described above.
 (b) providing at least one, or a plurality of, indicia associated with said array as described above.
 (c) providing a test compound. The test compound may be a member of a library of test compounds, and may be any suitable compound such as a protein, peptide or oligonucleotide (e.g., a DNA or RNA, such as mRNA); and then
 (d) detecting the binding of said test compound to at least one of said plurality of different oligonucleotides (e.g., by contacting the test compound to the array); and then
 (d) detecting determining the degree of binding (including simply the presence or absence of binding) of the test compound to one or more oligonucleotides on the array from (i) said detected binding and (ii) said indicia recording the presence of insufficient deprotection or insufficient elongation. Thus, insufficient deprotection or insufficient elongation of oligonucleotides in one or more locations in the array may be compensated for during the determining step. Such compensation may be achieved by any means, including ignoring particular separate and discrete regions on the array (e.g., in favor of other separate and discrete regions of the array that contain the same oligonucleotide). In another example, if one or more locations contain insufficient deprotection or elongation such that binding to those locations is reduced, the binding data derived from an experiment with that array can be adjusted upwards for those locations to indicate greater binding than that which would otherwise be indicated without the control made possible by the recorded indicia. The detecting or determining step may be carried out by any suitable means, such as generating a color indication of degree of binding, generating a numeric indication of degree of binding, generating a graphic or other symbolic indication of degree of binding, etc. The degree of binding may be an indication of binding is binding affinity, binding amount, or both binding affinity and binding amount, but is typically an indication of the amount of test compound that binds to a particular separate and discrete region of the array.

The present invention is explained in greater detail in the following non-limiting Examples.

EXAMPLE 1

Synthesis of Oligonucleotides

Synthesis was performed on an ABI DNA/RNA Synthesizer, Model 394 (PE Biosystems, 850 Lincoln Centre Drive, Foster City, Calif. 94404) according to manufactories protocol. Slightly modified 1 micromolar scale cycle was used during synthesis (see manufacturer's instructions). The primary starting materials (and suppliers/manufacturers in parentheses) were as follows:

Activator (0.45 M tetrazole in acetonitrile), CAP A (acetic anhydride/tetrahydrofuran/2,6 lutidine), CAP B (N-methylimidazole/tetrahydrofuran) and oxidizer (0.02 M iodine/pyridine/THF/H2O) (Prime Synthesis)

Pac-dA (5'-dimethoxytrityl-N-phenoxyacetyl-2'-deoxy-Adenosine,3'-[(2-cyanoethyl)-(N,N-diisopropyl)]-phosphoramidite (Glen Research)

Ipr-Pac-dG (5'-dimethoxytrityl-N-p-isopropyl-phenoxyacetyl-2'-Guanosine,3'-[(2-cyanoethyl)-(N,N-diisopropyl)]-phosphoramidite (Glen Research)

Ac-dC (5'-dimethoxytrityl-acetyl-2'-deoxycytidine,3'-[(2-cyanoethyl)-(N,N-diisopropyl)]-phosphoramidite (Glen Research)

dmf-G (5'-dimethoxytrityl-dimethylformamidine-Guanosine,2'-O-TBDMS-3'-[(2-cyanoethyl)-(N,N-diisopropyl)]-phosphoramidite (Glen Research)

Bz-dC—CPG beads (5'-dimethoxytrityl-N-benzoyl-2'-deoxycytidine, 3'-[(2-cyanoethyl)-(N,N-diisopropyl)]-phosphoramidite-succinyl linker-beads (3000 Ang) (CPG Inc.)

Ibu-dG—CPG beads (5'-dimethoxytrityl-N-isobutyl-2'-deoxycytidine,3'-[(2-cyanoethyl)-(N,N-diisopropyl)]-phosphoramidite-succinyl linker-beads (3000 Ang) (CPG Inc.)

The following compounds were synthesized, the compounds being linked to beads as shown:

Pac-dA—Pac-dA—Bz-dC—succinyl linker—Beads
Pac-dA—Pac-dA—Ibu-dG—succinyl linker—Beads
Ipr-Pac-dG—Ipr-Pac-dG—Bz-dC—succinyl linker—Beads
Ipr-Pac-dG—Ipr-Pac-dG—Ibu-dG—succinyl linker—Beads
Ac-dC—Ac-dC—Bz-dC—succinyl linker—Beads
Ac-dC—Ac-dC—Ibu-dG—-succinyl linker—Beads
dmf-G—dmf-G—Bz-dC—succinyl linker—Beads
dmf-G—dmf-G—Ibu-dG—succinyl linker—Beads The foregoing compounds were administered directly to animals as an immunogen, without separating the oligonucleotide from the solid support, for the production of antibodies, as further described in Example 2 below.

EXAMPLE 2

Inoculation of Animals

Female BALB/c mice of eight to twelve weeks old were purchased from Charles River, Raleigh, N.C., USA. The mice were housed in cases with filter caps.

After oligonucleotide chain synthesis was completed as described in Example 1, the beads with nucleotides were gently crushed by hand-pressuring the glass plates, between which beads were positioned.

5 µM of each eight oligonucleotides mentioned above were mixed in 4 ml PBS (150 mM sodium chloride in 100 mM phosphate buffer, pH 7.2).

The mixture was thoroughly vortexed suspending the crushed beads. 150 µL of the vortexed mixture was taken and added into 300 µL of PBS in a syringe. Just before injection, the solution containing beads was mixed again by shaking the syringe to suspend the broken beads. Then 150 µL or 300 µL of well-mixed solution was injected into mouse peritoneal cavity. This procedure was used for the first injection and the following boosts.

Injection Time Schedule:

| Injection | Date (day) |
|---|---|
| first | 0 |
| second | 14th |
| third | 28th |
| 4th | 42nd |
| 5th | 56th |
| 6th | 70th |
| 7th | 84th |
| 8th | 98th |
| 9th | 112th |
| 10th | 138th |
| 11th (final, 4 day before fusion) | 142nd |

Four days after the final injection, spleen cells are harvested from the animals and fused with myeloma cells (P3x.63.Ag8.653) in accordance with known techniques to produce hybridoma cell lines, which are then screened to determine the binding characteristics as described below to isolate particular cell lines that produce the desired antibody of the invention.

EXAMPLE 3

Immunodot-Blot Assay for Antibody Characterization

The Immunodot-blot assay involves UV cross linking of oligonucleotides onto membrane paper, and is directly applicable to a test kit for detection, identification and quantifying the protecting groups on product oligomers. This procedure may be carried out as follows: (a) wet membrane paper with TBS (10 mM Tris, pH 7.2; 150 mM NaCl); (b) blot oligonucleotides to be tested onto membrane paper under vacuum; (c) UV cross link nucleotide onto membrane paper; (d) block membrane paper with 1% casein-TBST (TBS plus Tween 20, 0.1% by volume) at room temperature for 2 hr or 4° C. overnight; (e) wash membrane with TBST 3 times, each for 15 min; (f) form antigen-antibody complex by incubation of plate with sample be tested (diluted in 1% casein-TBST) at room temperature for 1 hr; (g) wash as above; (h) react with second antibody conjugate (diluted in 1% casein-TBST) at room temperature for 1 hr; (i) wash as above; (j) develop color reaction by incubation of membrane with substrate solution.

EXAMPLE 4

Dot-Blot Assay of Monoclonal Antibody 1 H11

Monoclonal antibody 1 H11, produced as described in Example 2 above, was characterized by a dot-blot assay as described in Example 3 above. Results are shown as a bar graph in FIG. 1. In FIG. 1, lanes (or columns) 1 and 2 represent oligoPac-dA20mers treated with $NH_4OH$ for 6 hours at 65° C. and 15 minutes at 4° C., respectively. Columns 3 and 4 represent oligoBz-dC20mers treated with $NH_4OH$ for 6 hours at 65° C. and 15 minutes, respectively. Columns 5 and 6 represent oligoAc-dC20mers treated with $NH_4OH$ for 6 hours at 65° C. and 15 minutes, respectively. Columns 7 and 8 represent oligoIpr-Pac-dG20mers treated with $NH_4OH$ for 6 hours at 65° C. and 15 minutes, respectively. Columns 9 and 10 represent oligoIbu-dG20mers treated with $NH_4OH$ for 6 hours at 65° C. and 15 minutes, respectively. Columns 11, 12 and 13 represent oligodT20mers, completely deprotected, with DMT group only, and with cyanoethyl group only, respectively. Antibody activity is given as optical density (479 nm) from ELISA (Example 7 below), and the positive or negative result of the dot blot assay is given in the open or filled circle appearing over each column in the bar graph. Note the activity of monoclonal antibody 1 H11 in selectively binding to the oligoIbu-dG20mer in column 10.

EXAMPLE 5

Dot-Blot Assay of Monoclonal Antibody 7 H3

Monoclonal antibody 7 H3, produced as described in Example 2 above, was characterized by a dot-blot assay as described in Example 3 above. Results are shown as a bar graph in FIG. 1. In FIG. 1, lanes (or columns) 1 and 2 represent oligoPac-dA20mers treated with $NH_4OH$ for 6 hours at 65° C. and 15 minutes at 4° C., respectively. Columns 3 and 4 represent oligoBz-dC20mers treated with $NH_4OH$ for 6 hours at 65° C. and 15 minutes, respectively. Columns 5 and 6 represent oligoAc-dC20mers treated with $NH_4OH$ for 6 hours at 65° C. and 15 minutes, respectively. Columns 7 and 8 represent oligoIpr-Pac-dG20mers treated with $NH_4OH$ for 6 hours at 65° C. and 15 minutes, respectively. Columns 9 and 10 represent oligoIbu-dC20mers treated with $NH_4OH$ for 6 hours at 65° C. and 15 minutes, respectively. Columns 11, 12 and 13 represent oligodT20mers, completely deprotected, with DMT group only, and with cyanoethyl group only, respectively. Antibody activity is given as optical density as described above, and the positive or negative result of the dot blot assay is given in the open or filled circle appearing over each column in the bar graph. Note the activity of monoclonal antibody 1 H11 in selectively binding to the oligoBz-dC20mer in column 4.

EXAMPLE 6

Western Blot Assay for Antibody Characterization

The Western blot assay involves low voltage transfer of oligonucleotides from gel to membrane paper and UV cross linking of oligonucleotides onto the membrane. This assay may be carried out as follows: (a) cast 15% non-denaturing gel containing 10 mM MgCl; (b) load oligonucleotides (oligomers) into the wells of the gel; (c) run gel at 200 voltage in ice bath; (d) transfer oligonucleotides from gel to membrane paper at 25 voltage for 25 min in ice bath; (e) UV cross link polynucleotides on membrane; 69 block membrane paper with 1% casein-TBST at room temperature for 2 hr or 4° C. overnight; (g) wash membrane with TBST 3 times, each for 15 min; (h) incubate samples be tested (diluted in 1% casein-TBST) at room temperature for 1 hr; (i) wash as above; (j) incubate membrane with second antibody conjugate (diluted in 1% casein-TBST) at room temperature for 1 hr; (k) wash as above; and (l) color-develop by incubation of membrane with substrate solution.

EXAMPLE 7

Detection of Antibody Using Biotinylated Polynucleotides as Antigen and an ELISA Involving Streptavidin-Biotin System An enzyme-linked immunosorbent assay (ELISA) for the detection of the antibody is carried out as follows: (a) pre-screen microtiter plate that is pre-coated with streptavidin; (b) coat the plate with a preparation of biotinylated oligonucleotide or other materials to be tested (at 5 µg/ml in PBS)(PBS: 150 mM NaCl, 10 mM Phosphate buffer, pH 7.4), then incubate at room temperature for 2 hrs; (c) wash 3 times with 0.1% Tween in PBS (PBST), each for 15 min; (d) block with 1% casein in PBST at room temperature for hrs or 4° C. overnight; (e) wash as above; (f) form antigen-antibody complex by incubation of plate with antibody (or antibodies) at room temperature for 1 hr; (g) wash as above; (h) react with second antibody-peroxidase conjugate (in 1% casein-PBST) at room temperature for 1 hr; (i) wash as above; (j) develop color reaction by adding tetramethylbenzidine (TMB) solution (TMB solution: 42 mM TMB, 0.004% $H_2O_2$, 0.1 M acetate buffer, pH 5.6) and incubating at room temperature for 15 min, then stop the reaction with 2 M $H_2SO_4$; and (k) read absorption value at 469 nm.

EXAMPLE 8

Figure 3:
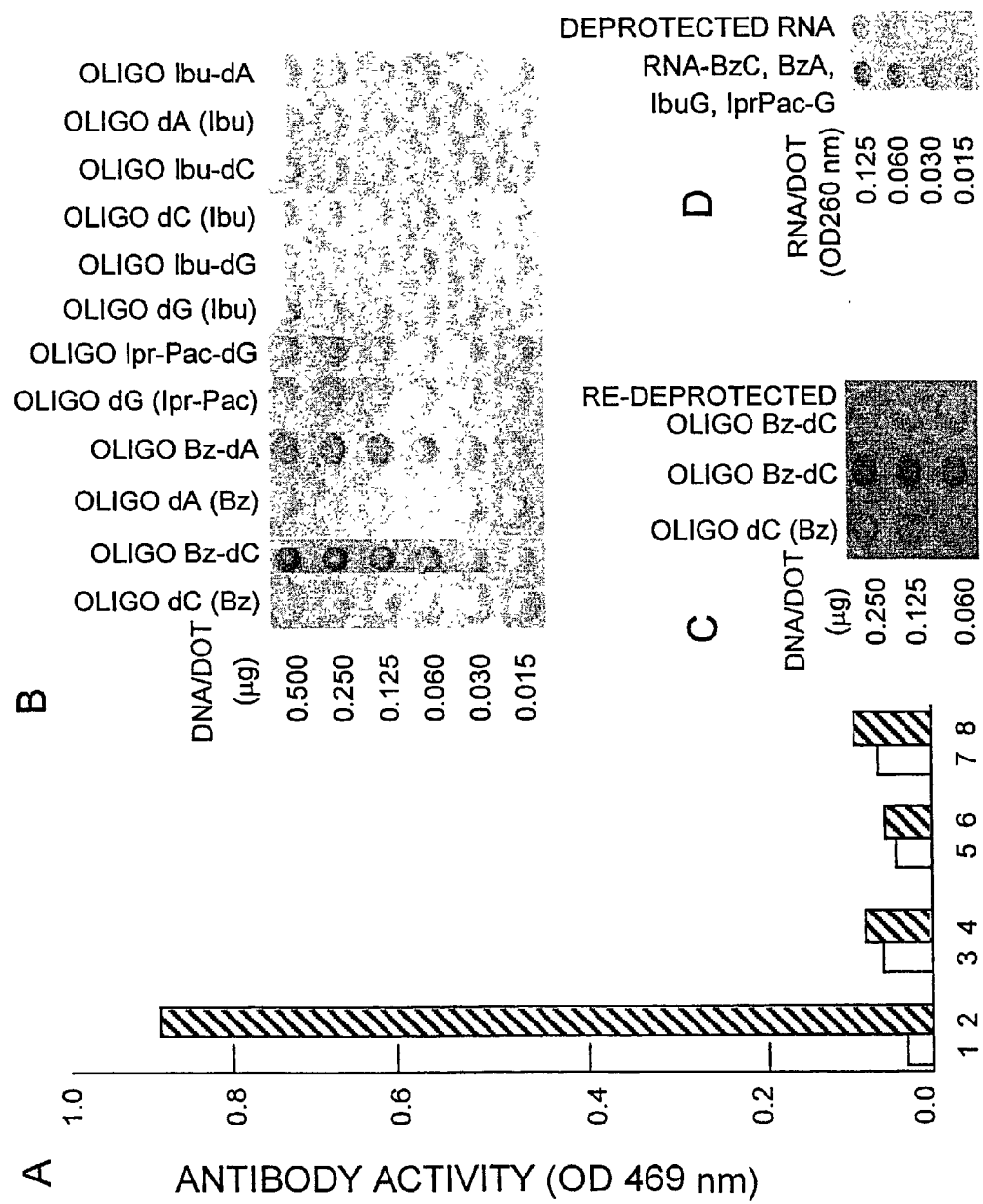
FIG. 3 shows ELISA (A) and dot-blot (B) results demonstrating specificity and detection sensitivity of a monoclonal antibody (mAb) of the commonly used protecting group, benzoyl (Bz), for the chemical synthesis of nucleic acids. Partially deprotected oligomer oligo Bz-dC (center column) can be re-treated to remove the remaining protecting groups, and re-tested with mAb (C). An RNA standard with protecting groups Bz, ibu and ipr-Pac was synthesized and assayed for identification of the protecting groups with the mAb against Bz (D).
Figure 4:
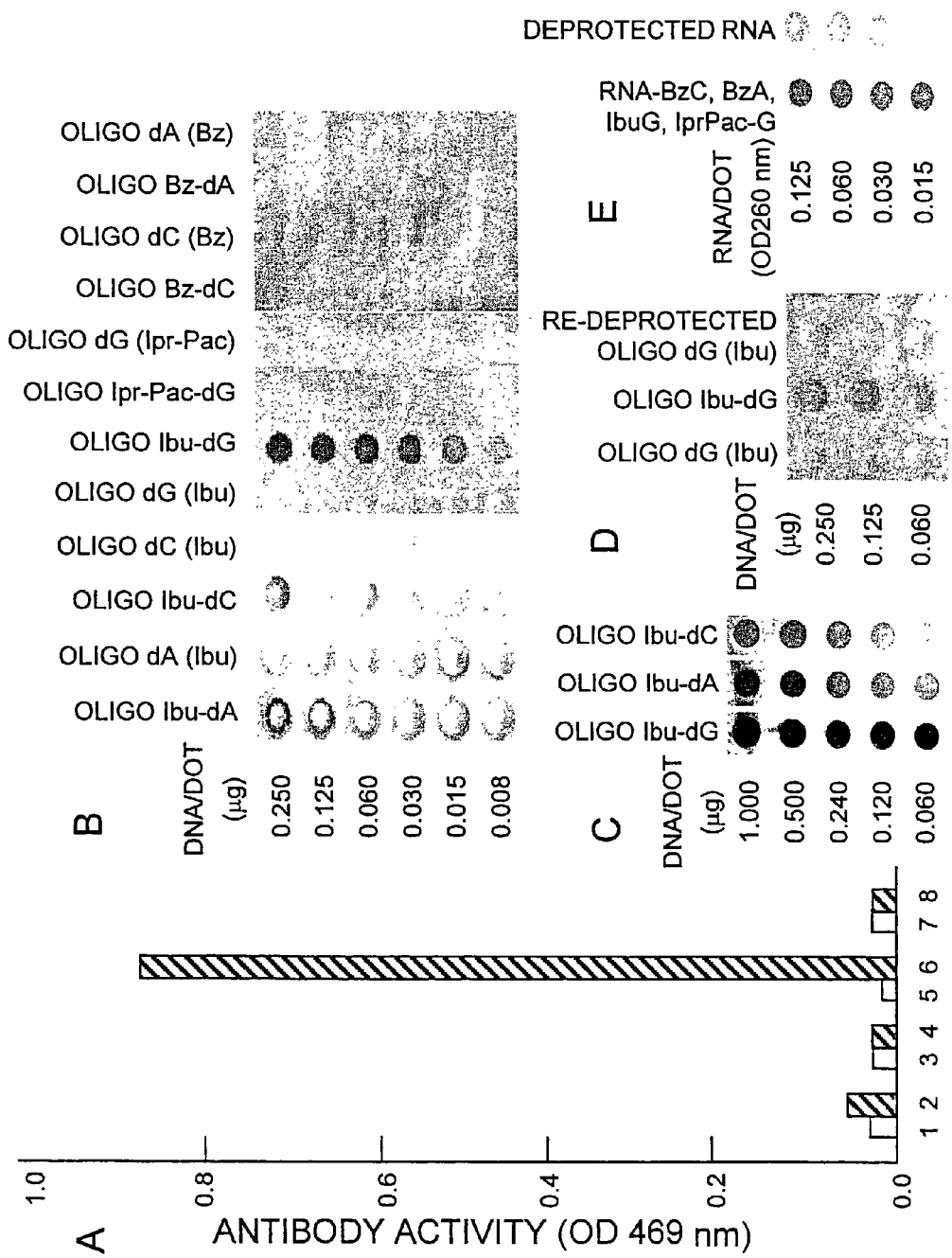
FIG. 4 shows ELISA (A) and dot-blot (B) results demonstrating specificity and sensitivity of a monoclonal antibody (mAb) and its detection of the commonly used protecting group, isobutyl (ibu), for the chemical synthesis of nucleic acids. Dot-blot assay with high amounts of DNA demonstrates that the ibu protecting group was recognized by the mAb no matter which nucleobase was protected (C). Partially deprotected oligomer oligo Bz-dC (center column) can be re-treated to remove the remaining protecting groups, and re-tested with mAb (D). An RNA standard with protecting groups Bz, ibu and ipr-Pac was synthesized and assayed for identification of the protecting groups with the mAb against ibu (E).
Figure 5:
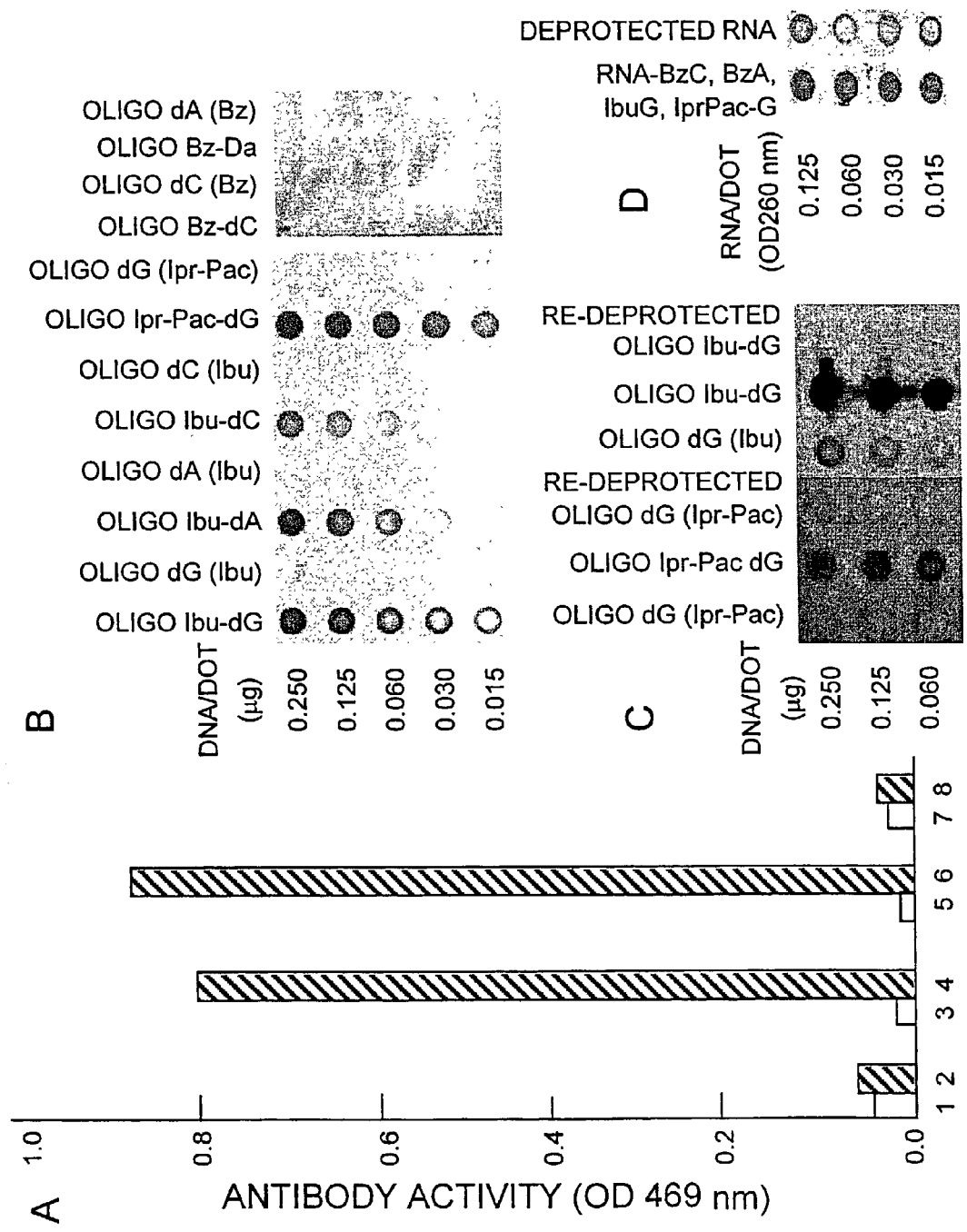
FIG. 5 shows ELISA (A) and dot-blot (B) results demonstrating specificity and sensitivity of a monoclonal antibody (mAb) and its detection of the commonly used protecting group, isopropylphenoxyacetyl (ipr-Pac), for the chemical synthesis of nucleic acids. Partially deprotected oligomers oligo ibr-Pac-dG and oligo ibu-dG (columns second from left and forth from left, respectively) can be re-treated to remove the remaining protecting groups, and re-tested with mAb (C). An RNA standard with protecting groups Bz, ibu and ipr-Pac was synthesized and assayed for identification of the protecting groups with the mAb against ipr-Pac (D).

ELISA and Dot-Blot Assay of Monoclonal Antibody Against Benzoyl, Isobutyryl, and Isopropylphenoxyacetyl Monoclonal antibodies (mAb) against protecting groups benzoyl (Bz), isobutyryl (ibu), and isopropylphenoxyacetyl (ipr-Pac), produced as described in Example 2 above, were characterized by a standard ELISA assay and a dot-blot assay as described in Example 3 above. An ELISA assay developed with biotinylated nucleic acids of 20 residues each attached to a 96-well microtiter plate demonstrated the specificity of the antibodies for their respective antigens. FIG. 3A, FIG. 4A, and FIG. 5A show results for monoclonal antibodies against Bz, ibu, and ipr-Pac, respectively. The figures show completely deprotected (<1% Bz remaining) homopolymers of dC residues, designated oligo dC(Bz), i.e. originally protected with Bz (lane 1, open bar), protected (>97% Bz remaining) oligo Bz-dC (lane 2, shaded bar), completely (<1% ipr-Pac remaining) deprotected oligo dG(ipr-Pac) (lane 3), protected (>76% ipr-Pac) oligo ipr-PacdG (lane 4), completely (<1% ibu remaining) deprotected oligo dG(ibu) (lane 5), protected (>91% ibu remaining) oligo ibu-dG (lane 6), and completely deprotected oligo dT (lane 7). The dT polymer had but one protecting group, dimethyltrityl (DMT) that was removed from the 5'OH of the 5'-terminal residue with mild acid. Finally, lane 8 of shows oligo dT with DMT remaining.

Dot-Blot assays of anti-Bz mAb, anti-ibu mAb, and anti-ipr-Pac mAb activities were performed in which the 20mer DNAs were linked to nitrocellulose membrane by UV. The amounts of 20mer DNA applied to the membrane are shown to the right of FIG. 3B, FIG. 4B, and FIG. 5B and demonstrate the level of sensitivity of the assay. The DNAs used to test anti-Bz mAb were those described for the ELISA plus deprotected oligo dA(Bz), protected oligo Bz-dA, oligo dC(ibu), oligo ibu-dC, oligo dA(ibu) and oligo ibu-dA. FIG. 3B shows that the anti-Bz mAb recognized the protecting group on dA and dC. The DNAs used to test anti-ibu mAB were those described for the ELISA plus protected oligo ibu-dA, deprotected oligo dA(ibu), oligo ibu-dC, oligo dC(ibu) and all are noted at the top of the dot-blot. FIG. 4B shows that the anti-ibu mAb recognized ibu on dG, the most common use of the protecting group, but also on dA. The DNAs used to test anti-ipr-Pac mAb were those described for the ELISA plus protected oligo ibu-dA, deprotected oligo dA(ibu), oligo ibu-dC, oligo dC(ibu), oligo Bz-dA, oligo dA(Bz) and all are noted at the top of the dot-blot. FIG. 5B shows that the anti-ipr-Pac mAb recognized ipr-Pac on dG, the most common use of the protecting group, but also on dA and dC. The mAb also recognized the ibu protecting group (ibu-dG, ibu-dA and ibu-dC). This cross-reactivity indicates that the antibody was highly selective in its identification of a chemistry common to both ipr-Pac and ibu, possibly $CH(CH_3)_2$. Thus the anti-ibu and anti-iprPac mAbs could be used in combination to identify the protecting group remaining on an oligo.

Greater amounts of DNA were tested in a dot blot assay of anti-ibu mAb (FIG. 4C). The results of this experiment demonstrated that the ibu protecting group was recognized by the mAb no matter which nucleobase was protected.

FIG. 3C, FIG. 4D, and FIG. 5C demonstrate that partially deprotected oligomers can be re-treated to remove the remaining protecting groups, and re-tested with mAb. FIG. 3C shows that anti-Bz mAb recognized re-deprotected oligomer oligo Bz-dC (center column). Likewise, FIG. 4D shows that anti-ibu mAb recognized re-deprotected oligomer oligo ibu-dG (center column) and FIG. 5C shows that anti-ipr-Pac mAb recognized re-deprotected oligomers oligo ipr-Pac-dG and oligo ibu-dG (columns second from left and forth from left, respectively). Thus, this approach is applicable to quality control without having to discard expensive nucleic acid samples.

An RNA standard with protecting groups Bz, ibu and ipr-Pac was synthesized and assayed for identification of the protecting groups with the mAb against Bz (FIG. 3D), ibu (FIG. 4E), and ipr-Pac (FIG. 5D). Dot-blot assays clearly show that the monoclonal antibodies do not differentiate RNA from DNA. Although there was a higher background signal with RNA than with DNA, there was a significant distinction between RNA with and without protecting groups, especially at the lower amounts of RNA. The amount of RNA on the membrane was estimated from the optical absorbance of the sample.

EXAMPLE 9 mAb Dot-Blot Assay of Protecting Groups vs HPLC

Figure 6:
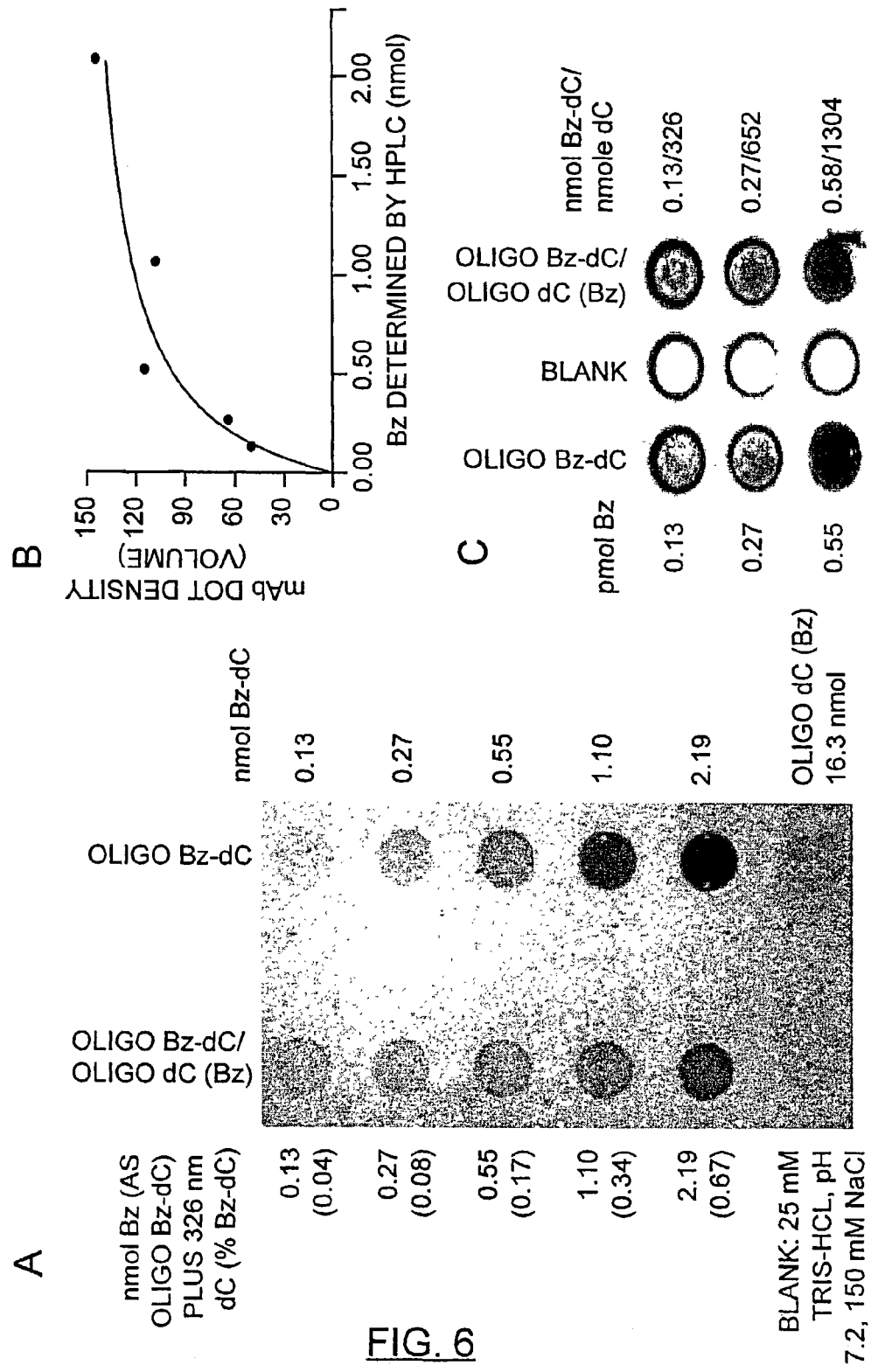
FIG. 6 shows a mAb dot-blot assay of protecting groups demonstrating the sensitivity and quantifiable response of the technology as related to HPLC. Dot-blot detection of Bz groups remaining on a standardized 20 mer oligo dC molecule was analyzed (A) and a quantitation of the mAb response (B) was determined. The mAb response was analyzed with an increase in the amount of DNA on the dot-blot membrane (C). The column on the left is just the protected Bz-dC 20 mer. The column on the right is the protected Bz-dC together with a 2500-fold excess of the completely deprotected oligo dC(Bz).
Figure 7:
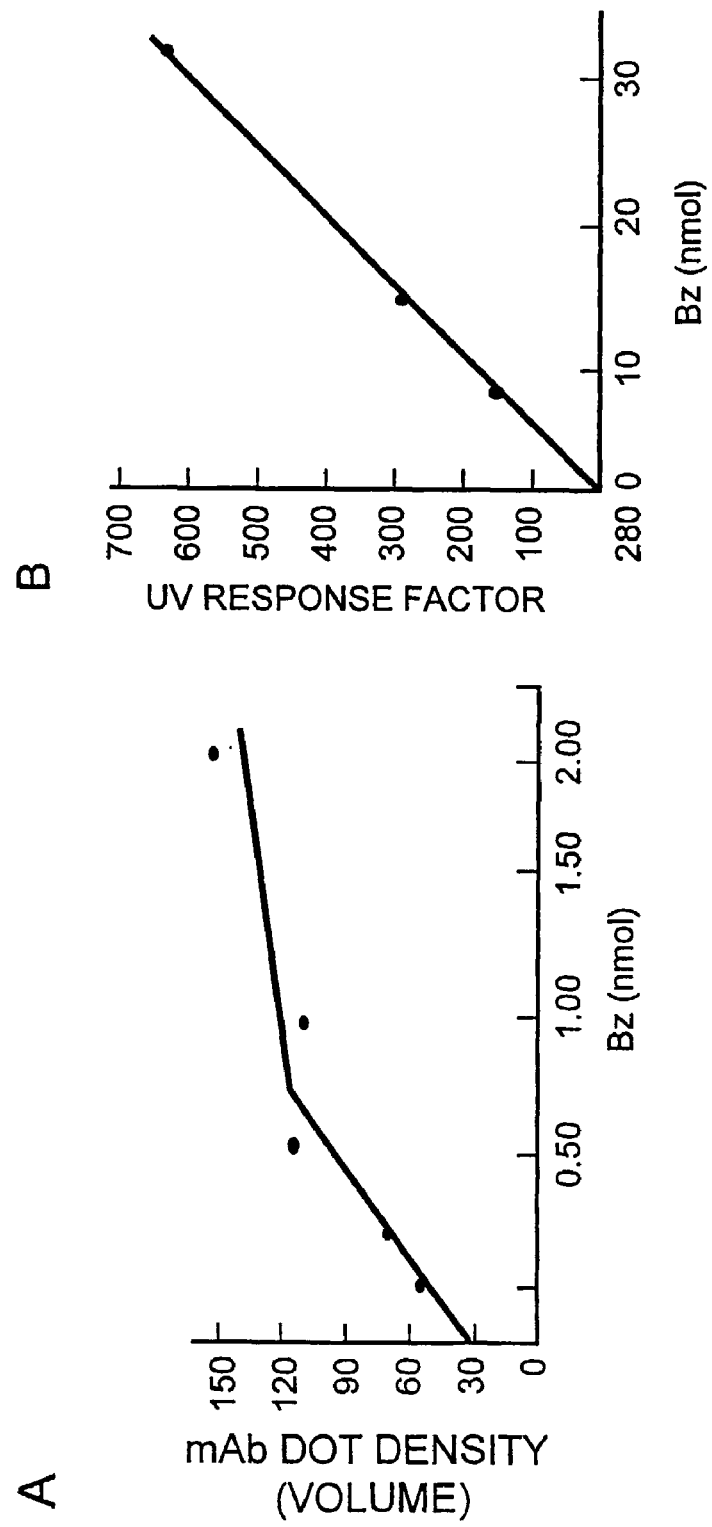
FIG. 7 shows a direct comparison of the mAb and HPLC detection of Bz in the pmole (A) and nmol range (B), respectively.

Dot-blot detection of Bz groups remaining on a standardized 20mer oligo dC molecule were performed as described in Example 3. Completely deprotected and the untreated oligo dC 20mers were analyzed for the Bz protecting group using a totally independent and different quantification method. The two oligomers were hydrolyzed to the constituent nucleosides and then their nucleoside composition identified and quantified using a recognized high performance liquid chromatography (HPLC) method with concentrated samples. Because of the lack of sensitivity, HPLC detection required 50-100 fold the amounts of Bz-dC used in the mAb assays (see FIG. 7). FIG. 6A shows the result of anti-Bz mAb tested against nmole amounts of Bz groups on protected oligo Bz-dC (right column) and the same nmole amounts of Bz- on Bz-dC (left column). Each amount of Bz-dC oligo was diluted with completely deprotected dC oligo of the same length (20mer) to demonstrate the sensitivity of the mAb detection even in the presence of 2500-fold dC (i.e. 0.04%). The mAb assay demonstrated that the mAb could detect the Bz group on DNA even in the presence of a 2500-fold excess of dC in DNA.

The dot-blot shown in FIG. 6A was subjected to densitometry to quantitate the mAb response. After background subtraction, the remaining density was plotted as a function of Bz groups in oligo Bz-dC determined by HPLC (FIG. 6B). The data indicated that the high sensitivity of the anti Bz mAb detection was linear in 0.1-1.0 mmol range.

Next, it was determined whether the mAb response could be enhanced with an increase in the amount of DNA on the dot-blot membrane. The amount of Bz was determined by standard HPLC methods. This experiment showed that detection of the Bz protecting group in a mixture of the protected sample with the deprotected sample at a ratio of 1/2500 could be enhanced by increasing the amount of DNA on the membrane, though the ratio was maintained (FIG. 6C).

Finally, experiments were conducted to show a direct comparison of the mAb and HPLC detection of Bz. Anti-Bz mAb was utilized in a dot-blot assay to detect Bz on dC in the oligo Bz-dC (20mer). The density response of the Bz group detected Bz by the mAb assay and quantified by densitometry was plotted against the amount of Bz in the DNA on each dot (FIG. 7A). The amount of Bz in the DNA was calibrated by digestion of a large amount of DNA and analysis by HPLC identification and quantification of the Bz-dC mononucleoside. For HPLC experiments, three samples of Bz-dC oligo were hydrolyzed and analyzed for composition by HPLC. The response of the UV-diode array detector was plotted against the amount of Bz in the samples (FIG. 7B). The sample amounts were determined by comparison to samples "spiked" with known amounts of Bz-dC. The amounts of Bz-dC added to samples as spikes were from a weighed stock of Bz-dC. Thus, the HPLC response was calibrated with known amounts of Bz-dC. The results of these experiments show that the detection of Bz by anti-Bz mAb was within the pmole range whereas HPLC detection of Bz was limited to the mmole range.

EXAMPLE 10

Detection of Remaining Protecting Groups in Commercial Samples

Figure 8:
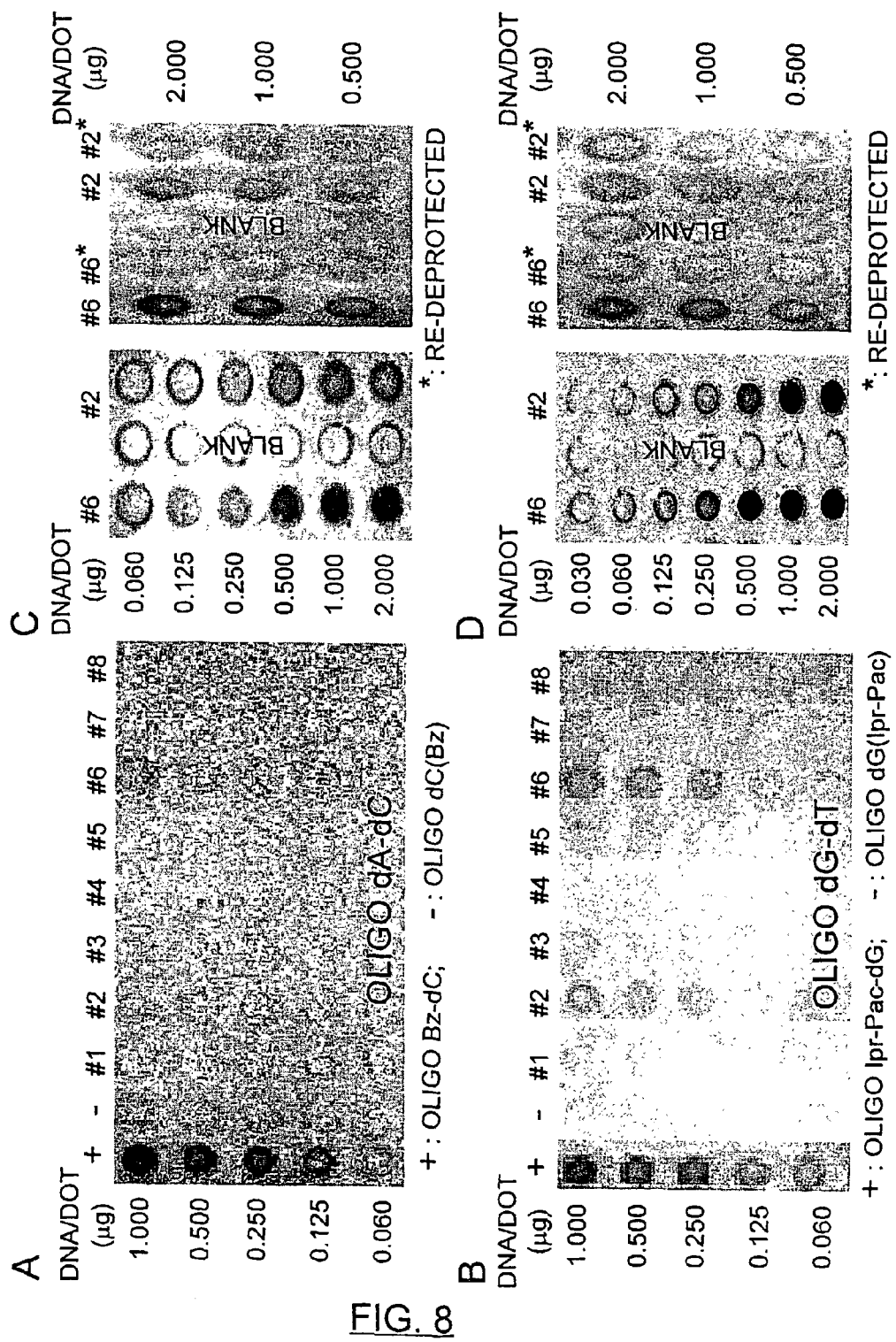
FIG. 8 shows a blind study demonstrating the detection of remaining protecting groups in commercial samples. dA-dC oligos were analyzed with anti-Bz mAb (A) and dG-dT oligos were analyzed with anti-ipr-Pac mAb (B). The oligo dA-dC samples from companies #2 and #6 were tested in higher amounts to confirm the presence of the Bz protecting group (C). In addition, the samples were treated to remove the remaining protecting groups using a standard protocol. The oligo dG-dT samples were assayed for the ipr-Pac protecting groups (D). The samples were re-treated to remove remaining protecting groups and re-analyzed as in (C).

A blind study was conducted to demonstrate the detection of remaining protecting groups in commercial samples by mAb. The purpose of the this experiment was to determine if protecting groups could be detected and identified with mAb technology in presumably completely deprotected samples that had been treated as commonly accomplished in the oligo synthesis industry. The nature of the protecting groups used by eight selected companies was not known, thus the experiment was a blind study. Two 20mer oligos (oligo dA-dC and oligo dG-dT) from each of the eight companies were ordered to be synthesized and deprotected, and salt removed under as identical conditions as possible. The oligos were shipped by express mail, as is often the case, and then subjected to mAb analysis by dot blot. The dA-dC oligo from one company (#6), and possibly a second (#2), had remaining Bz protecting groups as determined by anti-Bz mAb testing (FIG. 8A). The dG-dT oligos from two companies (#2 and #6) had ipr-Pac protecting groups remaining as determined by anti-ipr-Pac mAb (FIG. 8B). The remaining protecting groups in the commercial samples were confirmed by increasing amounts of sample and further deprotection and re-analyses. The oligo dA-dC samples from companies #2 and #6 were tested in higher amounts to confirm the presence of the Bz protecting group. In addition, the samples were treated to remove the remaining protecting groups using a standard protocol. The re-analysis after further deprotection indicated that the groups were now removed (FIG. 8C). This also demonstrates that expensive nucleic acid samples can be re-treated to remove protecting groups and that they need not be discarded. The oligo dG-dT samples were re-treated to remove remaining protecting groups and re-analyzed with anti-ipr-Pac mAb with the result that the ipr-Pac group could be removed without sacrificing the DNA (FIG. 8D).

EXAMPLE 11

Polyclonal Antibody Against Dimethyltrityl

Figure 9:
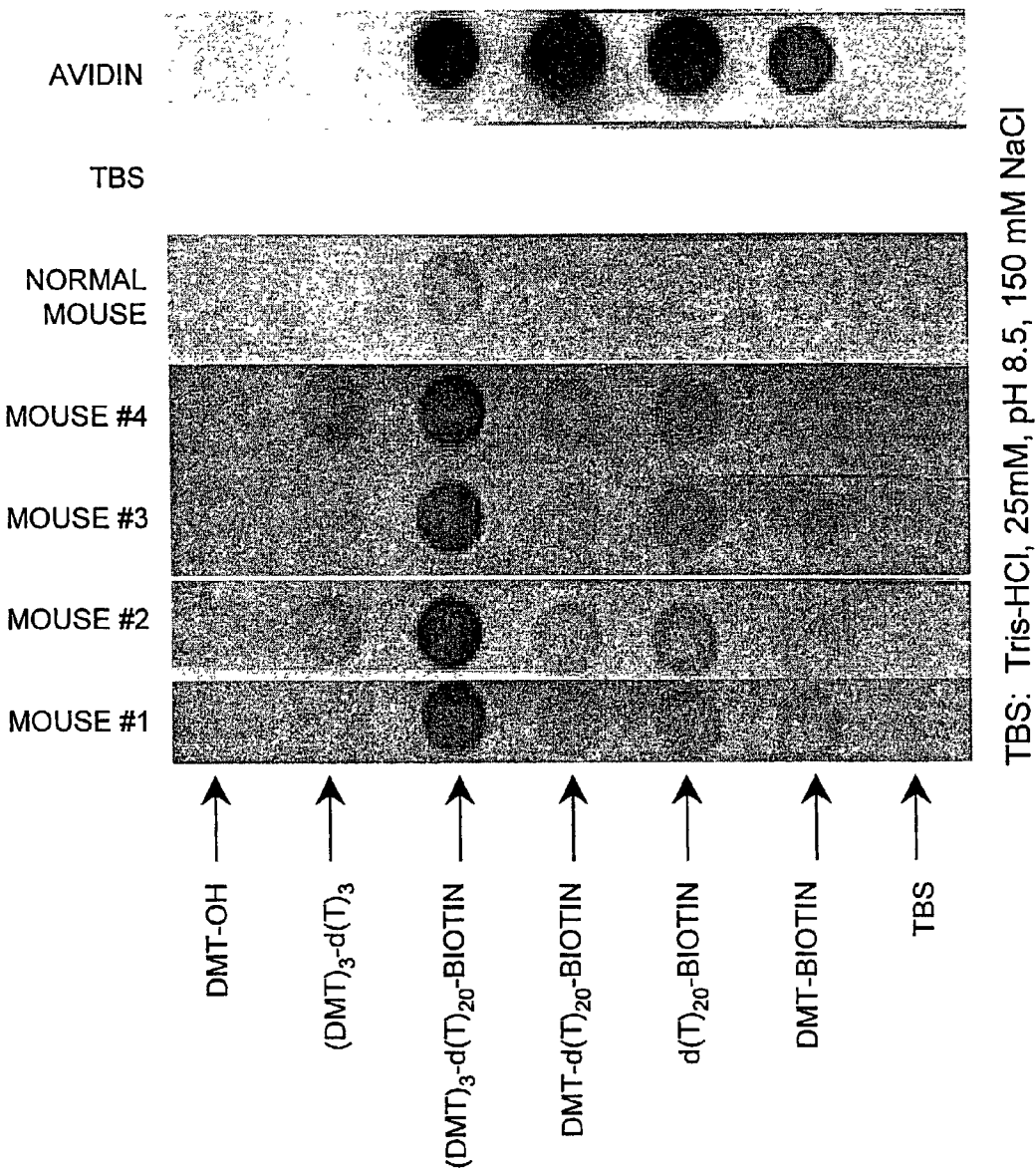
FIG. 9 shows the production and analyses of polyclonal antibody against the 5'terminal protecting group, dimethyltrityl (DMT).

Production and analyses of polyclonal antibody against the 5' terminal protecting group, dimethyltrityl (DMT) were as described in Example 2. Four mice were inoculated with DMT and sera were drawn from the mice after some weeks of boosting with antigen. DMT [DMT-OH], three DMT at the 5'-end of the deoxynucleotide trimer $d(T)_3$ [$(DMT)_3$-$d(T)_3$], three DMT at the 5'-end of the deoxynucleotide 20mer $d(T)_3$ with 3'-biotin [$(DMT)_3$-$d(T)_{20}$-biotin], one DMT at the 5'-end of the deoxynucleotide 20mer $d(T)_{20}$ with 3'-biotin [DMT-$d(T)_{20}$-biotin], the dT 20mer with 3'-biotin [$d(T)_{20}$-biotin], one DMT with biotin [DMT-biotin] and tris-borate saline control were applied to a nitrocellulose membrane that was then assayed with mouse sera (inoculated mice #1-4 and a control serum, normal) to assess anti-DMT antibody, mild acid to reveal presence of the DMT (TBS), and avidin to reveal the presence of biotin (FIG. 9). Sera from mice #2 and #4 recognized DMT [as $(DMT)_3$-$d(T)_3$], whereas mice #1, #3, and the normal mouse did not. Mild acid revealed the presence of DMT as a yellow color (not visible in figure) and avidin revealed the presence of biotin.

The foregoing is illustrative of the present invention, and is not to be construed as limiting thereof. The invention is defined by the following claims, with equivalents of the claims to be included therein.

That which is claimed is:

1. A method of screening an oligonucleotide array for insufficient deprotection or insufficient elongation of oligonucleotides therein, said method comprising the steps of:
    (a) providing an oligonucleotide array comprising a substrate having a plurality of different oligonucleotides immobilized thereon, with said different oligonucleotides immobilized in different separate and discrete locations on said substrate;
    (b) providing an antibody that specifically binds to a synthetic oligonucleotide having an organic protecting group covalently bound thereto, which antibody does not bind to said synthetic oligonucleotide when said organic protecting group is not covalently bound thereto; and then
    (c) contacting said antibody to said oligonucleotide array to thereby detect the presence or absence of binding of said antibody selected and discrete locations on said array, the presence of binding to separate and discrete locations in said array indicating insufficient deprotection or insufficient elongation of oligonucleotides therein.

2. A method according to claim 1, wherein said substrate comprises silicon.

3. A method according to claim 1, wherein said step of providing an array is carried out by synthesizing said oligonucleotides in situ on said substrate.

4. A method according to claim 1, further comprising repeating steps (b) to (c) at least once with a different antibody on each repetition so that a plurality of different protecting groups on oligonucleotides in the array may be detected.

5. A method according to claim 1, further comprising the step of:
  generating an indicia recording the presence of insufficient deprotection or insufficient elongation of oligonucleotides in at least one separate and discrete location on said array.

6. A method according to claim 5, wherein said indicia is a qualitative indicia.

7. A method according to claim 5, wherein said indicia is a quantitative indicia.

8. An oligonucleotide array, comprising, in combination:
  (a) a substrate having a plurality of different oligonucleotides immobilized thereon, with said different oligonucleotides immobilized in different separate and discrete locations on said substrate; and
  (b) a plurality of indicia associated with said array, said indicia recording the presence of insufficient deprotection or insufficient elongation of at least one oligonucleotide, each of said at least one oligonucleotide located in a different separate and discrete location on said array.

9. An array according to claim 8, wherein said substrate has at least 1000 different oligonucleotides immobilized in different separate and discrete locations on said substrate.

10. An array according to claim 8, wherein said indicia are stored in or printed on said array.

11. An array according to claim 8, wherein said indicia are contained in a computer file, said array further comprising an identifier associating said substrate and said indicia.

12. An oligonucleotide array, comprising, in combination:
  (a) a substrate having a plurality of different oligonucleotides immobilized thereon, with said different oligonucleotides immobilized in different separate and discrete locations on said substrate;
  (b) a plurality of indicia associated with said array, said indicia recording the presence of insufficient deprotection or insufficient elongation of at least one oligonucleotide, each of said at least one oligonucleotide located in a different separate and discrete location on said array; and
  wherein said indicia are contained on a web site, said array further comprising an identifier associating said substrate and said indicia.

* * * * *